US008399688B2

(12) United States Patent
Dumesic et al.

(10) Patent No.: US 8,399,688 B2
(45) Date of Patent: Mar. 19, 2013

(54) PRODUCTION OF LEVULINIC ACID, FURFURAL, AND GAMMA VALEROLACTONE FROM $C_5$ AND $C_6$ CARBOHYDRATES IN MONO- AND BIPHASIC SYSTEMS USING GAMMA-VALEROLACTONE AS A SOLVENT

(75) Inventors: James A. Dumesic, Verona, WI (US); David Martin Alonso, Madison, WI (US); Elif I. Gürbüz, Madison, WI (US); Stephanie G. Wettstein, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/445,643

(22) Filed: Apr. 12, 2012

(65) Prior Publication Data
US 2012/0302767 A1 Nov. 29, 2012

Related U.S. Application Data

(63) Continuation-in-part of application No. 13/327,468, filed on Dec. 15, 2011, which is a continuation-in-part of application No. 13/115,420, filed on May 25, 2011.

(51) Int. Cl.
*C07D 307/73* (2006.01)
*C07D 307/50* (2006.01)
*C07D 307/44* (2006.01)
(52) U.S. Cl. ........ 549/326; 549/489; 549/503; 562/515; 562/577
(58) Field of Classification Search .................. 549/325, 549/489, 503; 562/515, 577
See application file for complete search history.

(56) References Cited

U.S. PATENT DOCUMENTS 5,608,105 A 3/1997 Fitzpatrick

OTHER PUBLICATIONS

Alonso et al., Catalytic conversion of biomass to biofuels, *Green Chem.* 12, 1493-1513 (2010).
Bond et al., Integrated Catalytic Conversion of γ-Valerolactone to Liquid Alkenes for Transportation Fuels, *Science* 327, 1110-1114 (2010).
Bozell et al., Production of levulinic acid and use as a platform chemical for derived products, *Resour. Conserv. Recy.* 28, 227-239 (2000).
Bozell et al., Technology development for the production of biobased products from biorefinery carbohydrates—the US Department of Energy's "Top 10" revisited, *Green Chem.* 12, 539-554 (2010).
Bozell, J.J., Connecting Biomass and Petroleum Processing with a Chemical Bridge, *Science* 329, 522-523 (2010).
Braden, D.J., Thesis—Catalytic conversion of Lignocellulosic Biomass into Liquid Transportation Fuels: Fundamental and Applied Approaches, UW-Madison (2010).
Deng et al., Catalytic Conversion of Biomass-Derived Carbohydrates into γ-Valerolactone without Using an External $H_2$ Supply, *Angew. Chem. Int. Ed.* 48, 6529-6532 (2009).
Fegyverneki et al., Gamma-valerolactone-based solvents, *Tetrahedron* 66, 1078-1081 (2010).
Fellay et al., A Viable Hydrogen-Storage System Based on Selective Formic Acid Decomposition with a Ruthenium Catalyst, *Angew. Chem. Int. Edit.* 47, 3966-3968 (2008).
Geilen et al., Selective and Flexible Transformation of Biomass-Derived Platform Chemicals by a Multifunctional Catalytic System, *Angew. Chem. Inter. Ed.* 49, 5510-5514 (2010).
Heeres et al., Combined dehydration/(transfer)-hydrogenation of C6-sugars (D-glucose and D-fructose) to γ-valerolactone using ruthenium catalysts, *Green Chem.* 11, 1247-1255 (2009).
Horvat et al., Mechanism of Levulinic Acid Formation, *Tetrahedron Lett.* 26, No. 17, 2111-2114 (1985).
Horváth et al., γ-Valerolactone—a sustainable liquid for energy and carbon-based chemicals, *Green Chem.* 10, 238-242 (2008).
Huber et al., Raney Ni-Sn Catalyst for $H_2$ Production from Biomass-Derived Hydrocarbons, *Science* 300, 2075-2077 (2003).
Kirk-Othmer Encyclopedia of Chemical Technology (Ed Wiley, New York 2000), Alkylphenols, vol. 2, pp. 203-232.
Kunkes et al., Catalytic Conversion of Biomass to Monofunctional Hydrocarbons and Targeted Liquid-fuel Classes, *Science* 322, 417-421 (2008).
Lange et al., Towards "bio-based" Nylon: conversion of γ-valerolactone to methyl pentenoate under catalytic distillation conditions, *Chem. Commun.*, 3488-3490 (2007).
Lange et al., Valeric Biofuels: A Platform of Cellulosic Transportation Fuels, *Angew. Chem. Inter. Ed.* 49, 4479-4483 (2010).
Liu et al., The Effect if Flow Rate of Compressed Hot Water on Xylan, Lignin, and Total Mass Removal from Corn Stover, *Ind. Eng. Chem. Resear.* 42, 5409-5416 (2003).
Mehdi et al., Integration of Homogeneous and Heterogeneous Catalytic Processes for a Multi-step Conversion of Biomass: From Sucrose to Levulinic Acid, γ-Valerolactone, 1,4-Pentanediol, 2-methyl-tetrahydrofuran, and Alkanes, *Top. Catal.* 48, 49-54 (2008).
Prairie et al., A Fourier Transform Infrared Spectroscopic Study of $CO_2$ Methanation on Supported Ruthenium, *J. Catal.* 129, 130-144 (1991).
Riguetto et al., Ru-Sn catalysts for selective hydrogenation of crontonaldehyde: Effect of the Sn/(Ru + Sn) ratio, *Appl. Catal. Gen.* 318, 70-78 (2007).
Serrano-Ruiz et al., Conversion of cellulose to hydrocarbon fuels by progressive removal of oxygen, *Appl. Catal. B-Environ.* 100, 184-189 (2010).
Springerova et al., Selective hydrogenation of α,β-unsaturated carbonyl compounds on supported Ru-Sn catalysts, *Res. Chem. Intermediat.* 31, 785-795 (2005).
Yan et al., Synthesis of γ-Valerolactone by Hydrogenation of Biomass-derived Levulinic Acid over Ru/C Catalyst, *Energ. fuel* 23, 3853-3858 (2009).

*Primary Examiner* — Bernard Dentz
(74) *Attorney, Agent, or Firm* — Joseph T. Leone, Esq.; DeWitt Ross & Stevens S.C.

(57) ABSTRACT

A method to make levulinic acid (LA), furfural, or gamma-valerolactone (GVL). React cellulose (and/or other $C_6$ carbohydrates) or xylose (and/or other $C_5$ carbohydrates) or combinations thereof in a monophasic reaction medium comprising GVL and an acid; or (ii) a biphasic reaction system comprising an organic layer comprising GVL, and a substantially immiscible aqueous layer. At least a portion of the cellulose (and/or other $C_6$ carbohydrates), if present, is converted to LA and at least a portion of the xylose (and/or other $C_5$ carbohydrates), if present, is converted into furfural.

42 Claims, 14 Drawing Sheets

PRODUCTION OF LEVULINIC ACID, FURFURAL, AND GAMMA VALEROLACTONE FROM $C_5$ AND $C_6$ CARBOHYDRATES IN MONO- AND BIPHASIC SYSTEMS USING GAMMA-VALEROLACTONE AS A SOLVENT

CROSS-REFERENCE TO RELATED APPLICATIONS

This is a continuation-in-part of co-pending application Ser. No. 13/327,468, filed Dec. 15, 2011, which is a continuation-in-part of co-pending application Ser. No. 13/115,420, filed May 25, 2011, the contents of which are incorporated herein by reference.

FEDERAL FUNDING STATEMENT

This invention was made with government support under DE-FC02-07ER64494 awarded by the US Department of Energy and W911NF-09-2-0010 awarded by the ARMY/ARO. The government has certain rights in the invention.

BACKGROUND

Significant advances have been made in recent years with respect to using heterogeneous catalysts for converting biomass-derived compounds to fuels and chemicals. Conventional approaches deconstruct solid lignocellulose into smaller molecules that are soluble in various solvents (e.g., water, ionic liquids), thereby allowing transport of these reactants to the active sites on the heterogeneous catalyst, the majority of which are located within the pores of a high-surface area material. A difficulty in implementing this strategy is that chemical components used to deconstruct solid cellulose (e.g., sulfuric acid) may alter the performance of heterogeneous catalysts used subsequently to convert the soluble biomass-derived reactants to the desired fuels and/or chemicals. As a result, costly purification steps are required to implement a cascade catalytic process. Thus, the present method addresses a long-felt and unmet need by providing a route to levulinic acid, gamma-valerolactone, furfural, and downstream value-added chemicals that uses gamma-valerolactone itself as a reaction solvent in a monophasic reaction system and/or as an extraction solvent to extract levulinic acid and furfural from an aqueous solution in a biphasic reaction system.

In short, there is an increasing need for methods to produce fuels and chemicals from renewable, domestic sources to reduce the dependence on the fossil sources of carbon. A great many processes have been reported in the literature; however, scale-up of these processes to industrial scale has been severely hampered due to the necessity of purifying the final products and/or intermediates. Purification is often required to avoid negatively impacting downstream catalytic processes. Levulinic acid, for example, is a building block that can be upgraded to value-added chemicals and liquid transportation fuels by several pathways. Levulinic acid, however, is conventionally produced by cellulose deconstruction using dilute solutions of mineral acids. In conventional methods, the mineral acid needs to be removed prior to downstream processes, such as hydrogenation to gamma-valerolactone. If the acid is not removed, the downstream reactions are severely impacted or rendered infeasible.

In co-pending and co-owned application Ser. No. 13/115,420 is described a strategy that uses alkylphenols as a solvent for a biphasic extraction. Alkylphenols are insoluble in water, and thus separate from aqueous solutions of the cellulose deconstruction feed, while also extracting a portion of the levulinic acid. Even though alkylphenol extraction has significant advantages over previous processes, there are still some drawbacks. It uses an external solvent, requires final purification of the product by distillation, and has a moderate partition coefficient: approximately 2 for levulinic acid (concentration of levulinic acid in the organic phase divided by the concentration of levulinic acid in the aqueous phase). Also, the partition coefficient for formic acid (a co-product in the production of levulinic acid from cellulose) is less than 0.2. Thus, in the earlier process, formic acid cannot be used as internal source of $H_2$.

SUMMARY OF THE INVENTION

A first version of the invention is a method to make levulinic acid (LA), furfural, or gamma-valerolactone (GVL). This first version of the method comprises reacting in a first reactor a reactant comprising cellulose, hemicellulose, xylose (and/or other $C_5$ carbohydrates), glucose (and/or other $C_6$ carbohydrates) or combinations thereof in (i) a monophasic reaction medium comprising GVL and an acid; or (ii) a biphasic reaction system comprising an organic layer comprising GVL, and a substantially immiscible aqueous layer comprising water, an acid, and a sufficient concentration of a water-soluble solute to yield an aqueous solution that is substantially immiscible with the organic layer. At least a portion of the cellulose (and/or $C_6$ carbohydrates), if present, is converted to LA and at least a portion of the xylose (and/or other $C_5$ carbohydrates), if present, is converted into furfural.

More specifically described is a method to make levulinic acid (LA), furfural, furfuryl alcohol, or gamma-valerolactone (GVL). The method comprises reacting in a first reactor a reactant comprising $C_5$ carbohydrates, $C_6$ carbohydrates, cellulose, or hemicellulose, or combinations thereof in: (i) a monophasic reaction medium comprising GVL and an acid; or (ii) a biphasic reaction system comprising an organic layer comprising GVL, and a substantially immiscible aqueous layer comprising water, an acid, and a sufficient concentration of a water-soluble solute to yield an aqueous solution that is substantially immiscible with the organic layer. At least a portion of $C_5$ carbohydrates, if present in the reactant, is converted into furfural, and at least a portion of $C_6$ carbohydrates, if present in the reactant, is converted to LA.

The acid used preferably is independently selected from the group consisting of solid acids, hydrochloric acid, nitric acid, phosphoric acid, sulfuric acid, boric acid, hydrofluoric acid, trifluoroacetic acid, hydrobromic acid, acetic acid, oxalic acid, toluenesulfonic acid, and Lewis acids. The list of acids is for example only, and is non-limiting. Other acids may also be used, such as a solid acids, zeolites, etc.

The water-soluble solute in the biphasic reaction system is preferably a water-soluble salt, monosaccharide, disaccharide, or trisaccharide. Again, these are exemplary solutes. Other solutes may also be used in the method. Particularly preferred water-soluble solutes are sodium chloride and fructose. If sodium chloride is used, it is preferred that it be present in a concentration of from about 6 wt % to about 35 wt % (effectively the saturation point), based on the weight of the water in the aqueous solution.

At least a portion of any LA formed in the process may optionally be converted into GVL. This can be accomplished, for example, using a catalyst comprising one or more metals from Groups 6-14 of the periodic chart. Preferred catalysts are those comprising ruthenium, nickel, platinum, rhodium, tin, copper, and combinations thereof. Catalysts comprising ruthenium and tin are particularly preferred.

Optionally, at least a portion of any GVL formed in the process may be recycled back into the reactor.

At least a portion of any furfural formed in the process may optionally be converted into furfuryl alcohol. This can be accomplished using a catalyst comprising one or more metals from Groups 6-14 of the periodic chart, as noted previously. The method may further comprise converting at least a portion of any furfuryl alcohol formed into levulinic acid. Preferably this conversion is accomplished using a solid acid catalyst. Any of the other acid catalysts used herein may also be used.

In another version of the process, the reactant is reacted in a monophasic reaction medium, and further comprises separating at least a portion of the furfural, if present, from the reaction medium; and converting at least a portion of the LA, if present, into GVL. As noted previously, at least a portion of any furfural formed may be converted into furfuryl alcohol. Likewise, at least a portion of any furfuryl alcohol so formed may optionally be converted into levulinic acid. At least a portion of the GVL so formed may optionally be recycled back into the reactor.

Another version of the process comprises reacting the reactant in a first reactor in the monophasic reaction medium comprising GVL and an acid, wherein at least a portion of $C_5$ carbohydrates, if present in the reactant, is converted into furfural, and then transferring at least a portion of the monophasic reaction medium comprising GVL and an acid to a second reactor, wherein at least a portion of $C_6$ carbohydrates, if present in the reactant, is converted to LA. The acids recited above may be used.

Optionally, at least a portion of any furfural formed in the first reactor may be separated from the reaction medium before the reaction medium is transferred to the second reactor. Similar to previously described versions of the process, at least a portion of any furfural formed in the first reactor may optionally be converted into furfuryl alcohol before the reaction medium is transferred to the second reactor.

At least a portion of any furfuryl alcohol formed may optionally be converted into levulinic acid before the reaction medium is transferred to the second reactor. Likewise, at least a portion of any levulinic acid formed may optionally be converted into GVL before the reaction medium is transferred to the second reactor. At least a portion of the LA contained in the second reactor may optionally be converted into GVL (and partially recycled back into the reaction, as noted previously).

Another version of the invention comprises reacting the reactant in a first reactor in the biphasic reaction system, wherein at least a portion of any $C_5$ carbohydrates in the reactant is converted to furfural, and at least a portion of the furfural so formed partitions into the organic layer.

At least a portion of any furfural in the organic layer may optionally be separated from the organic layer. At least a portion of the furfural formed may optionally be converted into furfuryl alcohol (either in situ or after being separated from the organic layer). Similar to the other versions of the process, at least a portion of the furfuryl alcohol may optionally be converted into levulinic acid, and at least a portion of the levulinic acid optionally be converted into GVL.

Preferably the acids used in the various steps are independently selected from solid acids, mineral acids and/or organic acids, such as hydrochloric acid, nitric acid, phosphoric acid, sulfuric acid, boric acid, hydrofluoric acid, trifluoroacetic acid, hydrobromic acid, acetic acid, oxalic acid, toluenesulfonic acid, being Lewis or Bronsted acids. Among the solid acids, Amberlyst-brand resins, Nafion-brand resins, and zeolite solid acids are preferred. Preferred solid acids include A-70, Sulfated-zirconia, ZSM-5, sulfonated-carbon, mordenite, H-beta, and sulfonated-SBA-15.

When a biphasic system is used, the aqueous layer contains a water-soluble solute. It is preferred that the solute is a water-soluble salt, monosaccharide, disaccharide, or trisaccharide, such as (but not limited to) sodium chloride or fructose. Sodium chloride is preferred. If sodium chloride is used as a solute, it is preferably present in a concentration of from about 6 wt % to about 35 wt % (saturation), based on the weight of the water in the aqueous layer.

Optionally, at least a portion of the LA formed in the reaction, if present, may be converted into GVL. Additionally, if GVL is formed, an optional step is to recycle at least a portion of the GVL back into the reactor.

The LA may be converted into GVL using a hydrogenation catalyst. Any catalyst that will catalyze the hydrogenation of LA to GVL may be used, without limitation. Preferred catalysts include those comprising one or more metals from Groups 6-14 of the periodic chart. Particularly preferred catalysts are those comprising ruthenium, nickel, platinum, rhodium, tin, copper, and combinations thereof. Catalysts comprising ruthenium and tin are also preferred.

In another version of the process, the reactant is reacted in a monophasic reaction medium, and at least a portion of the furfural, if present, is separated from the reaction medium. LA, if present in the product mix, is converted into GVL via hydrogenation. As noted earlier, the GVL may be used as the end product, or a portion of the GVL may be recycled back into the reactor.

Another version of the method comprises reacting in a first reactor one or more reactants comprising $C_6$ and $C_5$ carbohydrates, such as cellulose and hemicellulose, in the monophasic reaction medium comprising GVL and an acid, wherein at least a portion of the $C_5$ carbohydrates/hemicellulose/xylose in the first reactor is converted to furfural, and then transferring at least a portion of the monophasic reaction medium comprising GVL and an acid to a second reactor, wherein at least a portion of the $C_6$ carbohydrates/cellulose/glucose contained in the second reactor is converted to LA. The same acids lists above may be used. It is preferred, but not required, that at least a portion of the furfural formed in the first reactor is separated from the reaction medium before the reaction medium is transferred to the second reactor. Optionally, at least a portion of the LA contained in the second reactor may be converted into GVL. At least a portion of the GVL may optionally be recycled into the second reactor.

At least a portion of the furfural can be converted into furfuryl alcohol over hydrogenation catalysts. Any catalyst that will catalyze the hydrogenation of furfural to furfuryl alcohol may be used, without limitation. Preferred catalysts include those comprising one or more metals from Groups 6-14 of the periodic chart. Particularly preferred catalysts are those comprising ruthenium, nickel, platinum, rhodium, tin, copper, and combinations thereof. Catalysts comprising copper for a gas-phase reaction and platinum-tin for a liquid-phase reaction are also preferred.

At least a portion of the furfuryl alcohol can be converted over an acid catalyst into levulinic acid (in the presence of water) or levulinate esters (in the presence of alcohols). Preferably the acids used is independently selected from solid acids, mineral acids and/or organic acids, such as, hydrochloric acid, nitric acid, phosphoric acid, sulfuric acid, boric acid, hydrofluoric acid, trifluoroacetic acid, hydrobromic acid, acetic acid, oxalic acid, toluenesulfonic acid, being Lewis or Bronsted acids. Among the solid acids, Amberlyst-brand resins, Nafion-brand resins, and zeolite solid acids are preferred. Preferred solid acids include A-70 and ZSM-5. Again, at least a portion of the levulinic acid can be converted into GVL. A portion of the GVL may optionally be recycled into the first reactor.

Yet another version of the method comprises reacting in a first reactor one or more reactants comprising xylose (and/or other $C_5$ carbohydrates) or a combination of xylose (and/or other $C_5$ carbohydrates) and glucose (and/or other $C_6$ carbohydrates) in the biphasic reaction system, wherein at least a portion of the xylose (and/or other $C_5$ carbohydrates) is converted to furfural, and at least a portion of the furfural so formed partitions into the organic layer. Optionally, at least a portion of the furfural in the organic layer may be separated from the organic layer.

Again a portion of the furfural can be converted into furfuryl alcohol. At least a portion of the furfuryl alcohol can be converted into levulinic acid. At least a portion of the levulinic acid can be converted into GVL. A portion of the GVL may optionally be recycled into the first reactor.

In another version of the invention, xylose (and/or other $C_5$ carbohydrates) and glucose (and/or other $C_6$ carbohydrates) are processed simultaneously. In this version, the reactant comprises xylose (and/or other $C_5$ carbohydrates) and glucose (and/or other $C_6$ carbohydrates), at least a portion of the glucose (and/or other $C_6$ carbohydrates) is converted into LA, and the LA is separated from the furfural. Again a portion of the furfural can be converted into furfuryl alcohol. At least a portion of the furfuryl alcohol can be converted into levulinic acid. At least a portion of the levulinic acid can be converted into GVL. A portion of the GVL may optionally be recycled into the first reactor.

DETAILED DESCRIPTION

Figure 1:
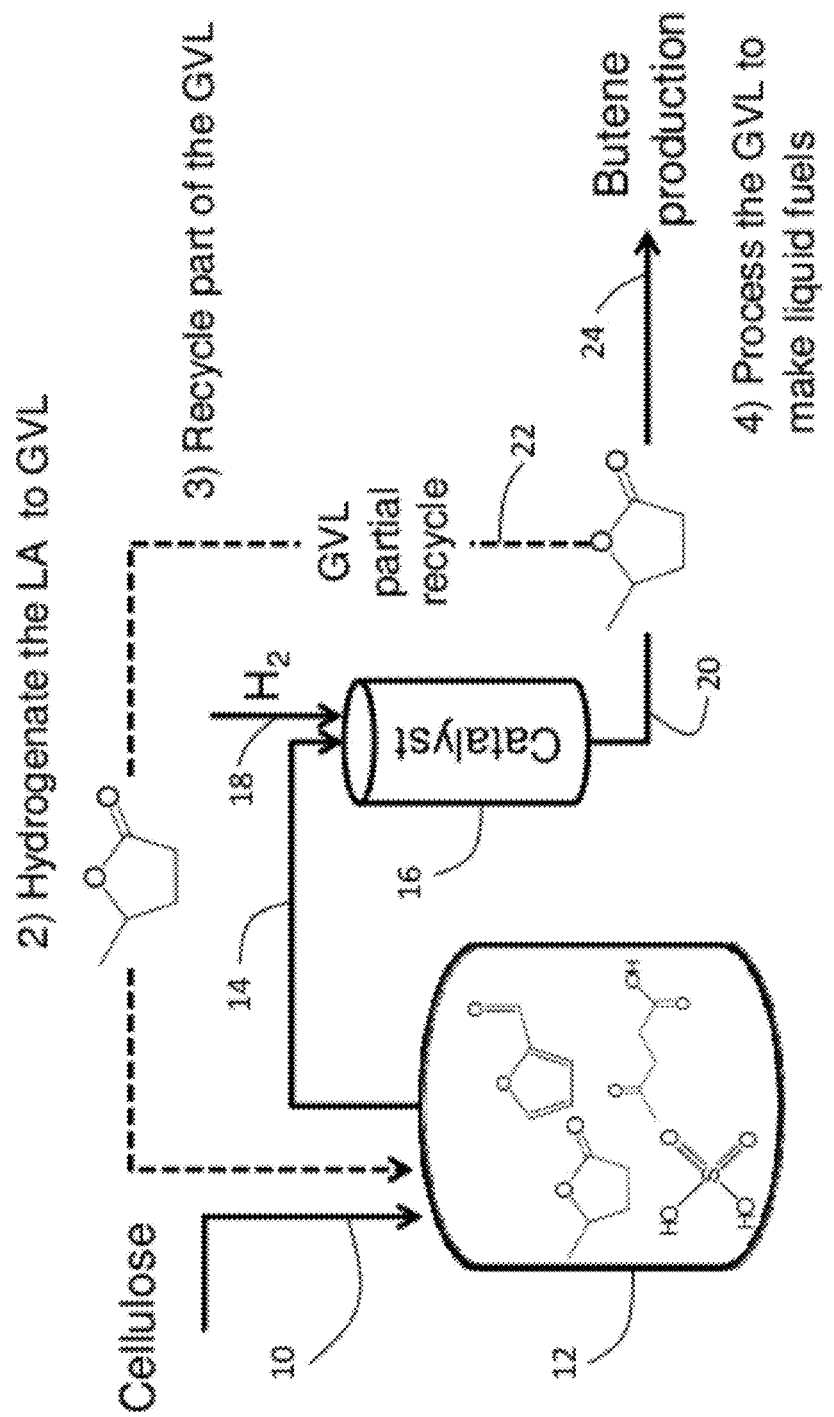
FIG. 1 is a schematic diagram depicting producing levulinic acid (LA) from cellulosic biomass or other sources of $C_6$ carbohydrates in a monophasic reaction solution comprising gamma valerolactone (GVL) and an acid catalyst (homogeneous or heterogeneous). The LA is hydrogenated into GVL, and a portion of the GVL is recycled back into the reaction chamber. Another portion of the GVL can be sold as the final product, or used to produce downstream chemicals, such as butene.

Abbreviations and Definitions:

"Biomass" as used herein includes materials containing cellulose, hemicellulose, lignin, protein and carbohydrates such as starch and sugar. Common forms of biomass include trees, shrubs and grasses, corn and corn husks as well as municipal solid waste, waste paper and yard waste. Biomass high in starch, sugar or protein such as corn, grains, fruits and vegetables, is usually consumed as food. Conversely, biomass high in cellulose, hemicellulose and lignin is not readily digestible by humans and is primarily utilized for wood and paper products, fuel, or is discarded as waste. "Biomass" as used herein explicitly includes branches, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, vines, hard and soft woods. In addition, biomass includes organic waste materials generated from agricultural processes including farming and forestry activities, specifically including forestry wood waste. "Biomass" includes virgin biomass and/or non-virgin biomass such as agricultural biomass, commercial organics, construction and demolition debris, municipal solid waste, waste paper, and yard waste. Municipal solid waste generally includes garbage, trash, rubbish, refuse and offal that is normally disposed of by the occupants of residential dwelling units and by business, industrial and commercial establishments, including but not limited to: paper and cardboard, plastics, food scraps, scrap wood, saw dust, and the like.

"Carbohydrate" is defined herein as a compound that consists only of carbon, hydrogen, and oxygen atoms, in any ratio.

"$C_5$ carbohydrate" refers to any carbohydrate, without limitation, that has five (5) carbon atoms. The definition includes pentose sugars of any description and stereoisomerism (e.g., D/L aldopentoses and D/L ketopentoses). $C_5$ carbohydrates include (by way of example and not limitation) arabinose, lyxose, ribose, ribulose, xylose, and xylulose.

"$C_6$ carbohydrate" refers to any carbohydrate, without limitation, that has six (6) carbon atoms. The definition includes hexose sugars of any description and stereoisomerism (e.g., D/L aldohexoses and D/L ketohexoses). $C_6$ carbohydrates include (by way of example and not limitation) allose, altrose, fructose, galactose, glucose, gulose, idose, mannose, psicose, sorbose, tagatose, and talose.

"Cellulose" refers to a polysaccharide of glucose monomers $((C_6H_{10}O_5)_n)$; "cellulosic biomass" refers to biomass as described earlier that comprises cellulose, and/or consists essentially of cellulose, and/or consists entirely of cellulose. Lignocellulosic biomass refers to biomass comprising cellulose, hemicellulose, and lignin. Lignocellulosic biomass comprises xylose, as does hemicellulose. For the experiments described below, microcrystalline cellulose (5% moisture, average size 20 μm) was obtained from Sigma-Aldrich, St. Louis, Mo. Dried corn stover was obtained through the Great Lakes Bioenergy Research Center, Madison, Wis., USA.

FA=formic acid. FID=flame ionization detector. GVL=γ-valerolactone. HPLC=high-performance liquid chromatography.

As used herein, the term "hydrogenation catalyst" refers without limitation to any catalyst, now known or developed in the future, homogenous or heterogeneous, that catalyzes the hydrogenation of carbonyl bonds (C═O). Preferred catalysts will reduce carbonyl bonds preferentially versus carbon-carbon double bonds (C═C). The activities need not be exclusive, but the chosen catalyst should catalyze the hydrogenation of C═O bonds at a rate much larger than the catalyst catalyzes the hydrogenation of C═C bonds. Catalysts comprising one or more metals from Groups 6-14 are preferred, also these metals doped with gallium, boron, germanium, indium and/or tin. Ruthenium, nickel, platinum copper, chromium and rhodium (alone, in combination, alloyed with other metals, and/or doped with gallium, germanium, indium and/or tin) are preferred. Other hydrogenation catalysts may also be used, such as metal hydrides (e.g., $NaBH_4$), polyoxometalates, Raney Ni, Raney Cu, etc. The catalysts may be used with or without a support.

Selective reduction may also be accomplished by transfer hydrogenation using a hydrogen donor. The term "hydrogen donor" refers to any compound with the ability to transfer a hydrogen atom to other substance. Exemplary hydrogen donors which can be utilized include, but are not limited to primary and secondary alcohols, polyols, olefins, cycloalkenes, carboxylic acids, and esters.

The rate of H-transfer can be increased by using homogeneous or heterogeneous catalysts. Exemplary catalysts include, but are not limited to, metals, zeolites, metal oxides supported or unsupported such as MgO, $ZrO_2$, gamma-$Al_2O_3$, $CeO_2$, $CeZrO_x$, $MgOAl_2O_3$, $Mg/Al/ZrO_x$, $MgO/SiO_2$, $CeO_2ZnO$, Sn-beta-zeolite, Ti-beta-zeolite, Sn-containing mesoporous silica, as well as metal salts and complexes of Pd, Pt, Ru, Ir, Rh, Fe, Ni, Co, Os, Mo. A full list of suitable hydrogen donors and catalysts can be found in R. A. W Johnsotne & A. H Wilby (1985) "Heterogeneous catalytic transfer hydrogenation and its relation to other methods for reduction of organic compounds," *Chem. Rev.* 85: 129-170, which is incorporated herein by reference.

FA=formic acid. GVL=gamma-valerolactone. HMF=hydroxymethylfurfural. LA=levulinic acid. SA=sulfuric acid. Mineral acid=any mineral-containing acid, including (by way of example and not limitation), hydrochloric acid, nitric acid, phosphoric acid, SA, boric acid, hydrofluoric acid, hydrobromic acid, and the like. Organic acid=any organic acid, without limitation, such as toluenesulfonic acid, FA, acetic acid, trifluoroacetic acid, oxalic acid, and the like.

Lewis Acid/Base=A Lewis acid is defined herein as any chemical species that is an electron-pair acceptor, i.e., any chemical species that is capable of receiving an electron pair, without limitation. A Lewis base is defined herein as any chemical species that is an electron-pair donor, that is, any chemical species that is capable of donating an electron pair, without limitation.

In preferred versions of the invention, the Lewis acid (also referred to as the Lewis acid catalyst) may be any Lewis acid based on transition metals, lathanoid metals, and metals from Group 4, 5, 13, 14 and 15 of the periodic table of the elements, including boron, aluminum, gallium, indium, titanium, zirconium, tin, vanadium, arsenic, antimony, bismuth, lanthanum, dysprosium, and ytterbium. One skilled in the art will recognize that some elements are better suited in the practice of the method. Illustrative examples include $AlCl_3$, $(alkyl)AlCl_2$, $(C_2H_5)_2AlCl$, $(C_2H_5)_3Al_2Cl_3$, $BF_3$, $SnCl_4$ and $TiCl_4$.

The Group 4, 5 and 14 Lewis acids generally are designated by the formula $MX_4$; wherein M is Group 4, 5, or 14 metal, and X is a halogen independently selected from the group consisting of fluorine, chlorine, bromine, and iodine, preferably chlorine. X may also be a psuedohalogen. Non-limiting examples include titanium tetrachloride, titanium tetrabromide, vanadium tetrachloride, tin tetrachloride and zirconium tetrachloride. The Group 4, 5, or 14 Lewis acids may also contain more than one type of halogen. Non-limiting examples include titanium bromide trichloride, titanium dibromide dichloride, vanadium bromide trichloride, and tin chloride trifluoride.

Group 4, 5 and 14 Lewis acids useful in the method may also have the general formula $MR_nX_{4-n}$; wherein M is Group 4, 5, or 14 metal; wherein R is a monovalent hydrocarbon radical selected from the group consisting of $C_1$ to $C_{12}$ alkyl, aryl, arylalkyl, alkylaryl and cycloalkyl radicals; wherein n is an integer from 0 to 4; and wherein X is a halogen independently selected from the group consisting of fluorine, chlorine, bromine, and iodine, preferably chlorine. X may also be a psuedohalogen. Non-limiting examples include benzyltitanium trichloride, dibenzyltitanium dichloride, benzylzirconium trichloride, dibenzylzirconium dibromide, methyltitanium trichloride, dimethyltitanium difluoride, dimethyltin dichloride and phenylvanadium trichloride.

Group 4, 5 and 14 Lewis acids useful in method may also have the general formula $M(RO)_nR'_mX_{(m+n)}$; wherein M is Group 4, 5, or 14 metal; RO is a monovalent hydrocarboxy radical selected from the group consisting of $C_1$ to $C_{30}$ alkoxy, aryloxy, arylalkoxy, alkylaryloxy radicals; R' is a monovalent hydrocarbon radical selected from the group consisting of $C_1$ to $C_{12}$ alkyl, aryl, arylalkyl, alkylaryl and cycloalkyl radicals; n is an integer from 0 to 4; m is an integer from 0 to 4 such that the sum of n and m is not more than 4; and X is a halogen independently selected from the group consisting of fluorine, chlorine, bromine, and iodine, preferably chlorine. X may also be a psuedohalogen. Non-limiting examples include methoxytitanium trichloride, n-butoxytitanium trichloride, di(isopropoxy)titanium dichloride, phenoxytitanium tribromide, phenylmethoxyzirconium trifluoride, methyl methoxytitanium dichloride, methyl methoxytin dichloride and benzyl isopropoxyvanadium dichloride.

Group 5 Lewis acids may also have the general formula $MOX_3$; wherein M is a Group 5 metal; X is a halogen independently selected from the group consisting of fluorine, chlorine, bromine, and iodine, preferably chlorine. A non-limiting example is vanadium oxytrichloride.

The Group 13 Lewis acids have the general formula $MX_3$; wherein M is a Group 13 metal and X is a halogen independently selected from the group consisting of fluorine, chlorine, bromine, and iodine, preferably chlorine. X may also be a psuedohalogen. Non-limiting examples include aluminum trichloride, boron trifluoride, gallium trichloride, indium trifluoride, and the like.

The Group 13 Lewis acids useful in method may also have the general formula: $MR_nX_{3-n}$ wherein M is a Group 13 metal; R is a monovalent hydrocarbon radical selected from the group consisting of $C_1$ to $C_{12}$ alkyl, aryl, arylalkyl, alkylaryl and cycloalkyl radicals; and n is an number from 0 to 3; and X is a halogen independently selected from the group consisting of fluorine, chlorine, bromine, and iodine, preferably chlorine. X may also be a psuedohalogen. Non-limiting examples include ethylaluminum dichloride, methylaluminum dichloride, benzylaluminum dichloride, isobutylgallium dichloride, diethylaluminum chloride, dimethylaluminum chloride, ethylaluminum sesquichloride, methylaluminum sesquichloride, trimethylaluminum and triethylaluminum.

Group 13 Lewis acids useful in this disclosure may also have the general formula $M(RO)_nR'_mX_{3-(m+n)}$; wherein M is a Group 13 metal; RO is a monovalent hydrocarboxy radical selected from the group consisting of $C_1$ to $C_{30}$ alkoxy, aryloxy, arylalkoxy, alkylaryloxy radicals; R' is a monovalent hydrocarbon radical selected from the group consisting of $C_1$ to $C_{12}$ alkyl, aryl, arylalkyl, alkylaryl and cycloalkyl radicals; n is a number from 0 to 3; m is an number from 0 to 3 such that the sum of n and m is not more than 3; and X is a halogen independently selected from the group consisting of fluorine, chlorine, bromine, and iodine, preferably chlorine. X may also be a psuedohalogen. Non-limiting examples include methoxyaluminum dichloride, ethoxyaluminum dichloride, 2,6-di-tert-butylphenoxyaluminum dichloride, methoxy methylaluminum chloride, 2,6-di-tert-butylphenoxy methylaluminum chloride, isopropoxygallium dichloride and phenoxy methylindium fluoride.

Group 13 Lewis acids useful in this disclosure may also have the general formula $M(RC(O)O)_nR'_mX_{3-(m+n)}$; wherein M is a Group 13 metal; RC(O)O is a monovalent hydrocarbacyl radical selected from the group consisting of $C_2$ to $C_{30}$ alkacyloxy, arylacyloxy, arylalkylacyloxy, alkylarylacyloxy radicals; R' is a monovalent hydrocarbon radical selected from the group consisting of $C_1$ to $C_{12}$ alkyl, aryl, arylalkyl, alkylaryl and cycloalkyl radicals; n is a number from 0 to 3 and m is a number from 0 to 3 such that the sum of n and m is not more than 3; and X is a halogen independently selected from the group consisting of fluorine, chlorine, bromine, and iodine, preferably chlorine. X may also be a psuedohalogen. Non-limiting examples include acetoxyaluminum dichloride, benzoyloxyaluminum dibromide, benzoyloxygallium difluoride, methyl acetoxyaluminum chloride, and isopropoyloxyindium trichloride.

The most preferred Lewis acids for use in the method are metal halides generally and more specifically transition metal halides, lathanoid metal halides, and Group 5, 13, and 14 metal halides. Preferred among the metal halides are metal chlorides. Preferred transition metal chlorides include, but are not limited to, $TiCl_4$, $VCl_3$ and the like. Preferred Group 13 and 14 metal halides and chlorides include, but are not limited to, $BF_3$, $AlCl_3$, $SnCl_4$, $InCl_3$, and $GaCl_3$. Preferred lanthanoid chlorides include, but are not limited to, $LaCl_3$, $DyCl_3$ and $YbCl_3$.

Mono-, di- and trisaccharides=a monosaccharide is a carbohydrate having the general formula $C_x(H_2O)_y$, where x and y are integers from 3 to about 8. Monosaccharides are classified by the number of carbon atoms they contain: diose (2) triose (3) tetrose (4), pentose (5), hexose (6), heptose (7), etc. Disaccharides and trisaccharides are dimers and trimers, respectively, of monosaccharides.

A "solid acid catalyst" can comprise one or more solid acid materials. The solid acid catalyst can be used independently or alternatively can be utilized in combination with one or more mineral acid or other types of catalysts. Exemplary solid acid catalysts which can be utilized include, but are not limited to, heteropoly acids, acid resin-type catalysts, mesoporous silicas, acid clays, sulfated zirconia, molecular sieve materials, zeolites, and acidic material on a thermo-stable support. Where an acidic material is provided on a thermo-stable support, the thermo-stable support can include for example, one or more of silica, tin oxide, niobia, zirconia, titania, carbon, alpha-alumina, and the like. The oxides themselves (e.g., $ZrO_2$, $SnO_2$, $TiO_2$, etc.) which may optionally be doped with additional acid groups such as $SO_4^{2-}$ or $SO_3H$ may also be used as solid acid catalysts.

Further examples of solid acid catalysts include strongly acidic ion exchangers such as cross-linked polystyrene containing sulfonic acid groups. For example, the Amberlyst®-brand resins are functionalized styrene-divinylbenzene copolymers with different surface properties and porosities. The functional group is generally of the sulfonic acid type. The Amberlyst®-brand resins are supplied as gellular or macro-reticular spherical beads. (Amberlyst® is a registered trademark of the Dow Chemical Co.) Similarly, Nafion®-brand resins are sulfonated tetrafluoroethylene-based fluoropolymer-copolymers which are solid acid catalysts. Nafion® is a registered trademark of E.I. du Pont de Nemours & Co.)

Zeolites may also be used as solid acid catalysts. Of these, H-type zeolites are generally preferred, for example zeolites in the mordenite group or fine-pored zeolites such as zeolites X, Y and L, e.g., mordenite, erionite, chabazite, or faujasite. Also suitable are ultrastable zeolites in the faujasite group which have been dealuminated.

TCD=thermal conductivity detector. WHSV=weight hour space velocity. XRD=X-ray diffraction.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, 5, 6, from 1 to 9, from 3.6 to 4.6, from 3.5 to 9.9, and so forth.

All references to singular characteristics or limitations shall include the corresponding plural characteristic or limitation, and vice-versa, unless otherwise specified or clearly implied to the contrary by the context in which the reference is made.

The processes described herein can be run in batch mode, semi-continuous mode, and/or continuous mode, all of which are explicitly included herein.

All combinations of method or process steps as used herein can be performed in any order, unless otherwise specified or clearly implied to the contrary by the context in which the referenced combination is made.

The methods described and claimed herein can comprise, consist of, or consist essentially of the essential elements and limitations of the disclosed methods, as well as any additional or optional ingredients, components, or limitations described herein or otherwise useful in synthetic organic chemistry.

Monophasic Conversion of Cellulosic Biomass (and/or Other $C_6$ Carbohydrates) to Levulinic Acid and Gamma-Valerolactone:

A first version of the disclosed method to yield levulinic acid (LA) and gamma-valerolactone (GVL) is schematically depicted in FIG. 1. Here, a feedstock 10 comprising cellulosic biomass or cellulose itself is introduced into a reaction vessel 12 containing an acidic solution of GVL. Any acid may be used to acidify the GVL reaction solution. Mineral acids and solid acid catalysts are preferred. The acidic GVL solution degrades/deconstructs the cellulose found in the feedstock 10 to yield LA. The digested solution, which contains LA and may contain homogeneous acids, is then isolated from the reaction solution via conduit 14. At this point, the LA present in the reaction solution may be concentrated, isolated, and/or purified and sold as the final product.

Alternatively, LA present in the product mix may be fed by conduit 14 into catalytic reactor 16, which contains a hydrogenation catalyst and may optionally include added molecular hydrogen via conduit 18. The LA present in the product mix will be hydrogenated in reactor 16 into GVL, which is removed from the reactor 16 at conduit 20. The method branches at this point. The entire amount of GVL produced may be sold as the final product, or used to produce other downstream products, such as the butene shown in the lower-right corner of FIG. 1 at conduit 24. Or, a portion of the GVL produced may be used as the final product (or for other purposes) as shown by 24 and another portion of the GVL recycled via conduit 22 into the reactor 12. In this fashion, GVL for use in reactor 12 is formed by the reaction itself.

The conditions in the reactor 12 and the catalyst in reactor 16 are preferably chosen to minimize the hydrogenation of GVL. The outlet 20 or reactor 16 is a stream of GVL that, as noted above, can be used as the final product chemical, or can be used to produce fuels as butene. If a mineral acid or other homogeneous acid is used in reactor 12, the acid may optionally be neutralized before the hydrogenation reaction. This is not required, but tends to increase the life of the hydrogenation catalyst present in reactor 16. Alternatively, catalysts tolerant to mineral acids (as RuRe) may be used in reactor 16. In that instance, the homogeneous acid is recycled along with the GVL solvent. If a solid acid catalyst is used in reactor 12, a filtration step (to retain the solid acid catalyst within reactor 12) maybe required before introducing the product stream from conduit 14 into the hydrogenation reactor 16.

The reaction solution present in reactor 12 comprises GVL, preferably comprises more than 50% (w/w) GVL, preferably more than 60% GVL, and more preferably still more than 70% GVL. The GVL solution may also comprise water.

Figure 9:
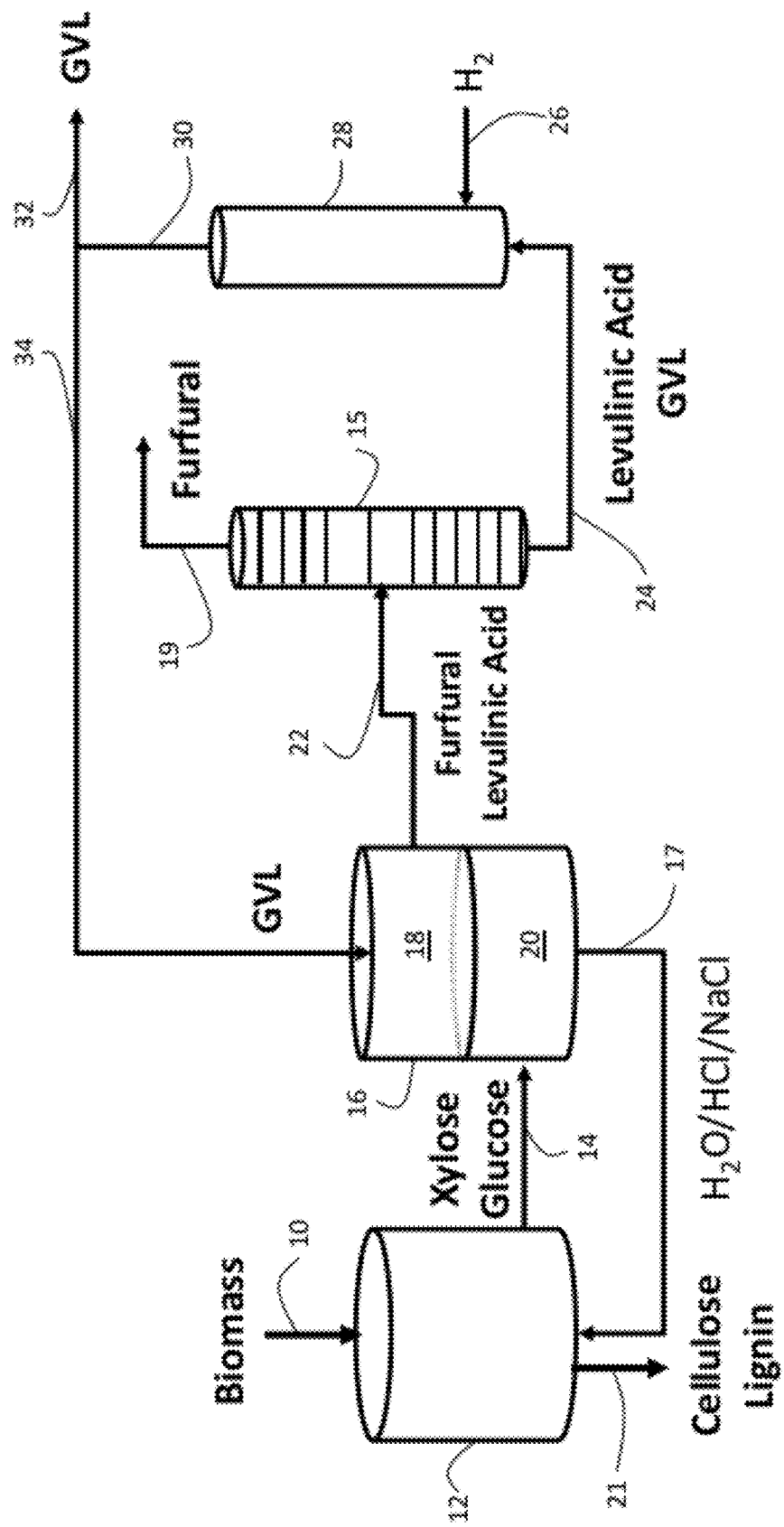
FIG. 9 is a schematic diagram showing one method for deconstructing biomass in a first monophasic reaction and then converting the resulting xylose (and/or other $C_5$ carbohydrates) and glucose (and/or other $C_6$ carbohydrates) into furfural and GVL, respectively, in a second, biphasic reaction. A portion of the GVL may be recycled back into reactor 16. The cellulose may then be used in other processes, such as paper making.
Figure 13:
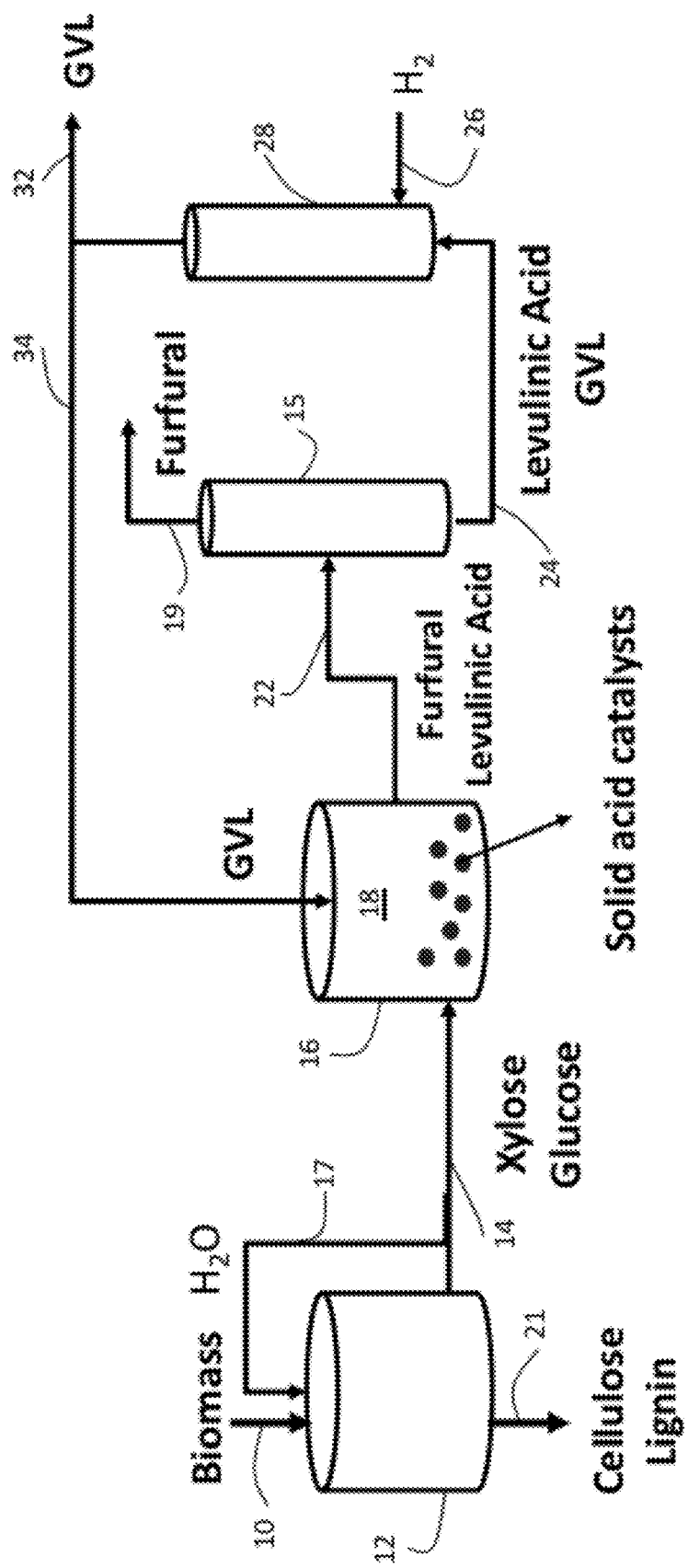
FIG. 13 is a schematic diagram illustrating converting biomass to furfural via a monophasic dehydration of xylose, in which the monophasic reaction solution comprises GVL.

Throughout the various schematic figures, LA is hydrogenated to GVL in reactor 16 (FIGS. 1-5) or reactor 28 (FIGS. 9 and 13). In each case, hydrogenation may be carried out in a flow reactor or a batch reactor. For continuous hydrogenation of the LA, the reaction may be accomplished in a fixed-bed reactor operating in an up-flow or down-flow configuration. Thus, in the experiments described herein, the catalyst was placed in a stainless steel tubular reactor (6.35 mm OD) and held between two end plugs of silica granules and quartz wool. The catalyst was reduced in-situ for 3 h at 450° C. (1° C. $min^{-1}$) before use. The feed was introduced into the reactor using an HPLC pump (Lab Alliance-brand Series I; Scientific System, Inc., State College, Pa., USA). The flow of $H_2$ during the reaction (25 $cm^3$(STP)/min) was controlled by a mass flow controller (Brooks Instrument, 5850S; Brooks Instrument, Inc., Hatfield, Pa., USA). The tubular reactor was fitted inside an aluminum block and placed within an insulated furnace (Applied Test Systems, Butler, Pa., USA). Bed temperature was monitored at the reactor wall using a Type K thermocouple (Omega Engineering, Inc., Stamford, Conn., USA) and controlled using a 16A series programmable temperature controller (Love Controls, Inc., Michigan City, Ind., USA). Reactor pressure (35 bar of $H_2$) was controlled using a back pressure regulator (model BP-60; GO Regulator, Inc, Spartanburg, S.C., USA). The reactor effluent flowed into a vapor-liquid separator wherein the liquid product was collected. For batch reactions, a 450 mL Parr Instruments Hastelloy C-276 batch reactor (Parr Instrument Company, Moline, Ill., USA), equipped with a variable speed mechanical stirrer, was loaded with 4 g of reduced and passivated Ru—Sn/C catalyst and the entering via conduit 14 (FIGS. 1-5) or conduit 24 (FIGS. 9 and 13). The system was purged with helium, pressurized to 24 bar with $H_2$ and heated to 180° C. (9° C. $min^{-1}$ ramp) with a high-temperature fabric heating mantle to reach a final pressure of 35 bar of $H_2$. The reactor was maintained at 180° C. overnight while stirring at 600 rpm. At the end of the reaction, the reactor was cooled and weighed.

Regarding the hydrogenation catalysts used in the experiments, a 5 wt % Ru/C was used as received from the vendor (Sigma-Aldrich). Ru—Sn/C catalyst was prepared by incipient wetness impregnation of the 5 wt % Ru/C catalyst with a solution of $SnCl_2.2H_2O$, which resulted in a final molar ratio Ru:Sn of 3.6:1. The catalyst was dried at 80° C. for 2 hours before loading into a flow reactor, or reduced for 3 h at 450° C. (1° C. $min^{-1}$) and passivated in 2% $O_2$/He for 3 hours before use in a batch reactor.

Fresh and spent RuSn/C samples were characterized by volumetric titration of exposed metal sites with carbon monoxide. Static chemisorption was carried out using a Micromeritics ASAP 2020 (Micromerimetrics Instrument Corp., Norcross, Ga., USA). Prior to analysis, catalyst samples were outgassed under vacuum at 303 K and subsequently reduced in flowing $H_2$ at 450° C. (80 cm$^3$(STP)/min $H_2$, 1.3° C. min$^{-1}$ heating rate, 240-min hold). The sample was then evacuated at 723 K for 60 min to remove adsorbed $H_2$ and cooled to 30° C. CO uptake was measured volumetrically at 30° C. through sequential doses at incrementing pressures to approximately 10 Torr. The sample was again evacuated at 303 K, and a second CO uptake isotherm was collected. Irreversible adsorption of CO was taken as the difference in uptake between the two isotherms, and dispersions were calculated by normalizing total CO uptake by total metal content (Ru plus Sn). The Ru—Sn/C catalyst initially undergoes deactivation, during which the rate of GVL production and LA conversion decrease in the first 100 h on stream. The catalyst then remains stable for more than 200 h. In the case of Ru/C, the catalyst showed continuous deactivation, with the rates of GVL production and LA conversion decreasing continuously after 200 h.

Experiments were carried out to explore the hydrolysis reaction in reactor 12. For example, mineral acids, such as HCl and $H_2SO_4$, and solid acid catalysts such as Amberlyst® 70 were tested, along with varying the amount of water in reactor 12. The GVL functions to solubilize the cellulose and any humins that form. Thus, at the end of a typical reaction there are no solids in the reactor 12. The experiments described in Tables 1-3 were carried out in 10 mL glass reactors in a pre-heated oil bath using magnetic stirring.

In a typical experiment, approximately 2 wt % solid cellulose was added to the reaction solution, with overall concentration of mineral acid of from 0.005 to 0.1 M. The GVL and water were added to the reactor 12 to reach the desired mass ratio. The reactor was placed in the oil bath, held for the stated time, then taken from the oil bath and cooled with an air line. A small portion of the solution was sampled. In all experiments, no solids remained in reactor 12 (presumably due to solubilization by the GVL).

Reducing the amount of water in the reaction vessel 12 generally increases the yield of LA at a given time (Table 1). Table 1 presents the yield of LA in a reaction performed in a reactor 12 as shown in FIG. 1, under the conditions stated in Table 1.

TABLE 1

LA yield as a function of water wt % in the reactor at a SA concentration of 0.05M, T = 170° C., Time = 16 h.

| Water (wt %) | LA Yield (%) |
| --- | --- |
| 10 | 55 |
| 20 | 36 |
| 30 | 26 |

As can be seen from Table 1, the yield of LA was markedly improved at 10% water in reactor 12, as compared to 20% or 30% water in the reactor. All other variables were the same in these reactions.

The experiments depicted in Table 2 show that the amount of acid required to drive the reaction of cellulose to LA is significantly reduced when using a reaction solvent comprising GVL.

TABLE 2

LA Yield as a Function of Acid Concentration

| SA Concentration (M) | T (° C.) | Time (h) | Water (wt %) | LA Yield (%) |
| --- | --- | --- | --- | --- |
| 0.5 | 155 | 6 | 100 | 55 |
| 0.01 | 155 | 16 | 10 | 58 |
| 0.005 | 155 | 16 | 10 | 60 |
| 0.005 | 170 | 3 | 10 | 46 |
| 0.005 | 170 | 16 | 10 | 53 |

As shown in Table 2, LA yield was highest for a 16-hour reaction that was 0.005 M acid and 10% water in GVL. High LA yield at low acid concentration is desirable because it minimizes the need to neutralize the product stream entering reactor 16 in the event an acid-sensitive hydrogenation catalyst is being used.

Table 3 shows the results of a series of experiments using different kinds of acids, including mineral acids and solid acids. As shown in the table, solid acid catalysts and mineral acid catalysts can both be utilized in the method and give similar final yields of LA.

TABLE 3

LA yield as a function of acid type using 2 wt % cellulose.

| Acid | T (° C.) | Time (h) | Water (wt %) | LA Yield (%) |
| --- | --- | --- | --- | --- |
| 6 wt % Amberlyst 70 | 170 | 16 | 10 | 62 |
| 2 wt % Amberlyst 70 | 155 | 8 | 0 | 21 |
| 2 wt % Amberlyst 70 | 155 | 24 | 100 | 0 |
| 0.01M HCl | 155 | 16 | 10 | 45 |
| 0.01M HCl | 155 | 24 | 10 | 65 |
| 0.01M SA | 155 | 16 | 19 | 58 |

Figure 2:
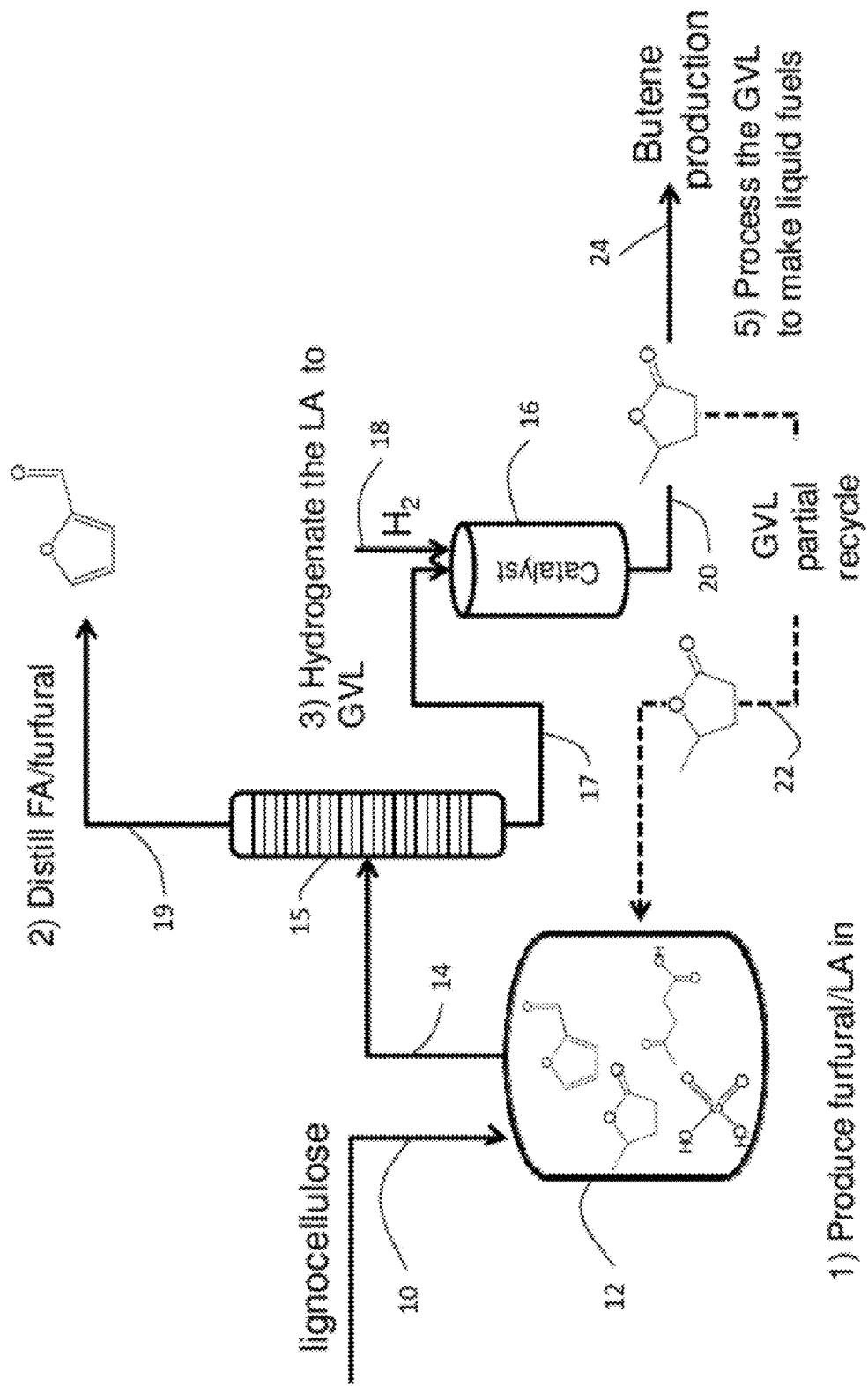
FIG. 2 is a schematic diagram depicting producing Furfural (Fur) and GVL simultaneously in a monophasic reaction solution comprising GVL as the solvent and an acid catalyst (homogeneous or heterogeneous). LA and Fur are formed in the monophasic reaction chamber 12. The Fur and formic acid (FA) are separated from the product mix, and the LA is hydrogenated into GVL. A portion of the GVL may be recycled into the reaction chamber. Another portion of the GVL can be sold as the final product, or used to produce downstream chemicals, such as butene.
Figure 3:
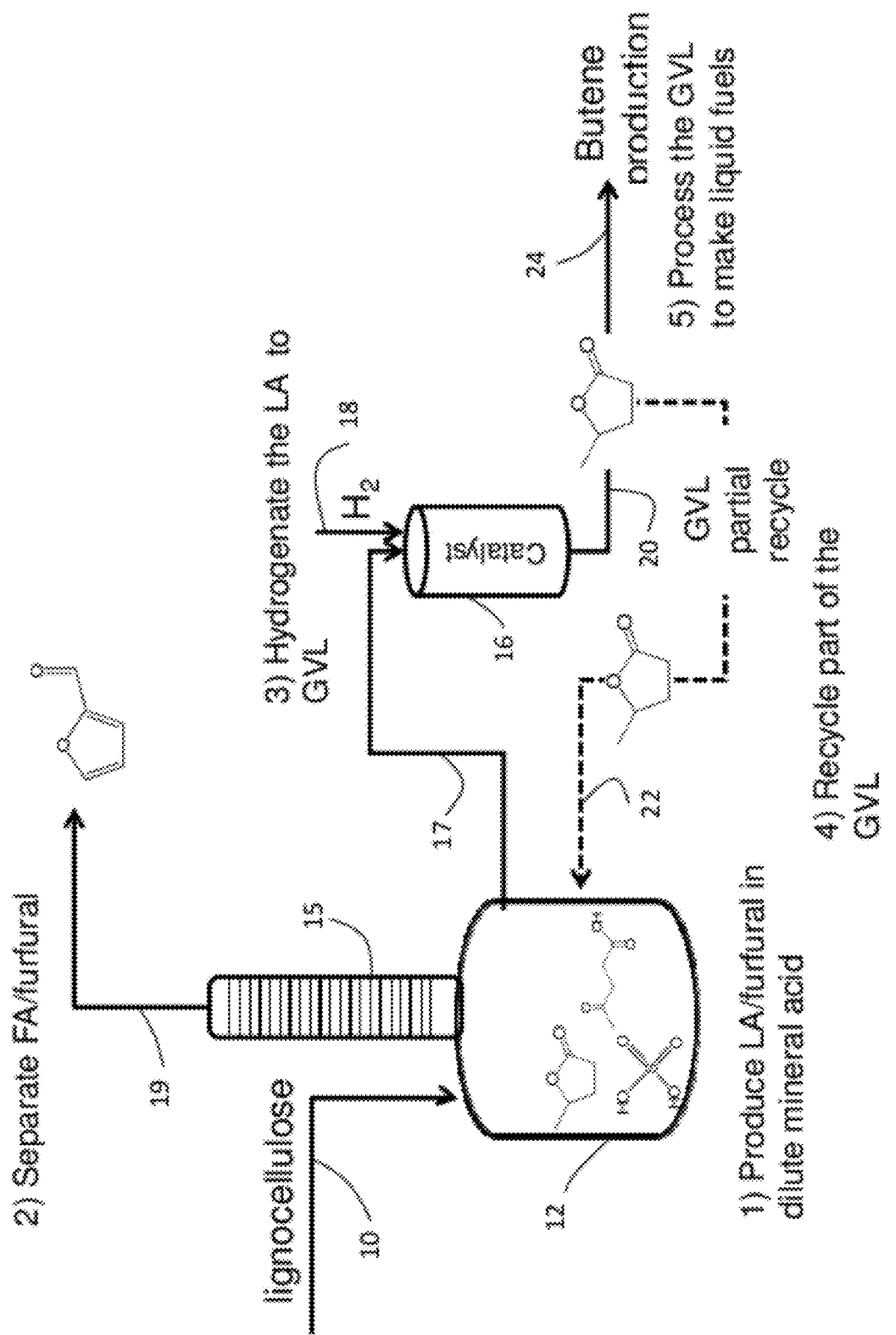
FIG. 3 is a schematic diagram illustrating a process very similar to that shown in FIG. 2, with the exception that the Fur and FA formed in monophasic reaction chamber 12 are removed via reactive distillation. That is, the distillation apparatus 15 is integrated into the reaction chamber 12.

Conversion of Lignocellulosic Biomass (and/or Other $C_6$ and $C_5$ Carbohydrates) to Levulinic Acid (LA), Furfural (Fur), Furfuryl Alcohol (FurA) and Gamma-Valerolactone (GVL):

FIGS. 2 and 3 depict another version of the invention in which lignocellulosic biomass or any other combination of $C_5$ and $C_6$ carbohydrates is converted to LA, Fur, and/or GVL in a monophasic reaction in which the solvent comprises GVL. The numbering in FIGS. 2 and 3 is identical, so the two figures shall be described jointly.

Figure 4:
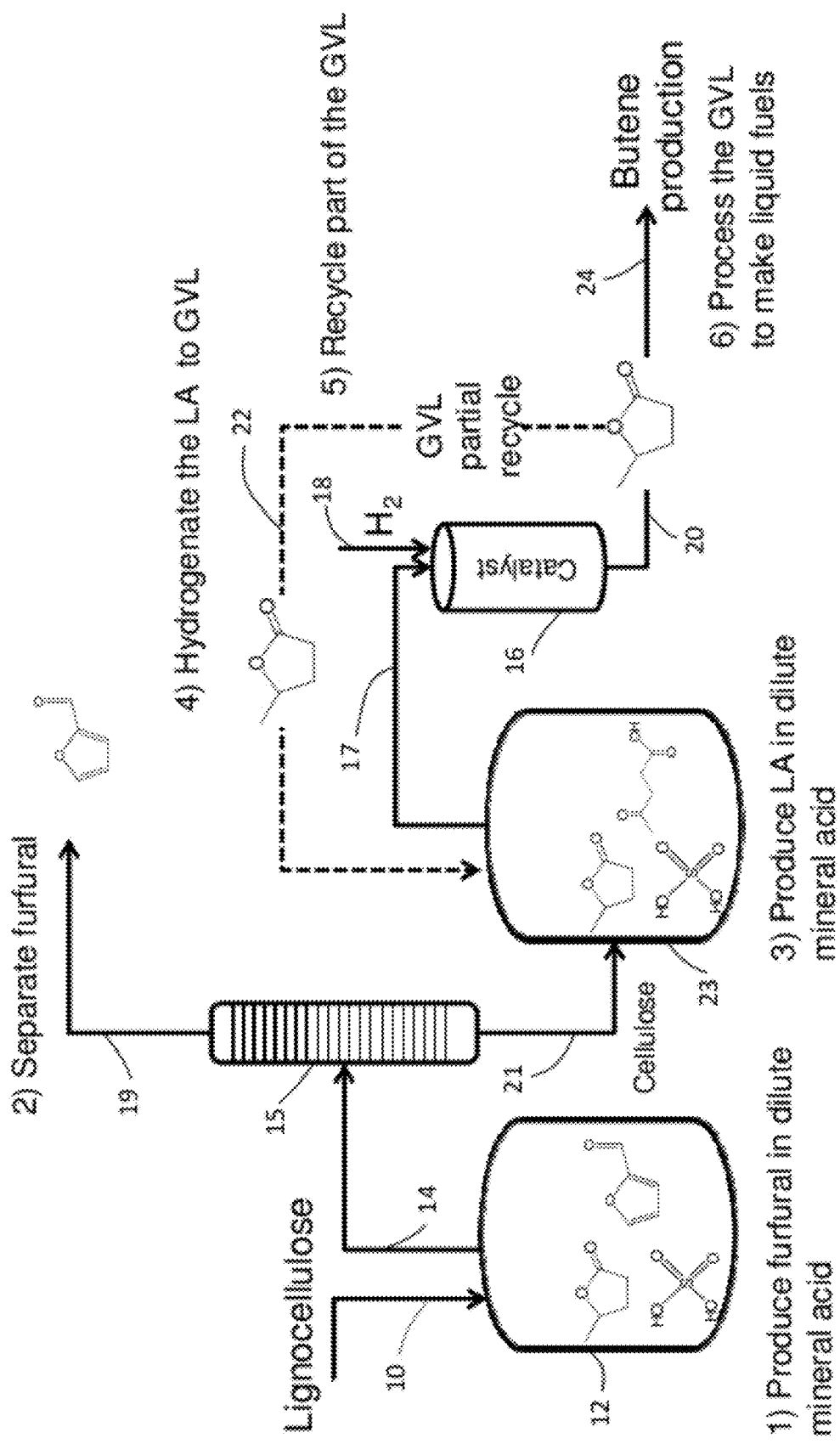
FIG. 4 is a schematic diagram illustrating two serial monophasic reactions in which xylose (or other $C_5$ carbohydrates) contained in lignocelullosic biomass is converted to Fur (in vessel 12) and the Fur is purified as a product, and the cellulosic/$C_6$ carbohydrate portion of the feed is converted to LA (in vessel 23), which is then hydrogenated into GVL. GVL is used as the solvent in both vessels.

Biomass such as corn stover contains both hemicellulose, which is comprised of xylose and other $C_6$ and $C_5$ carbohydrates and cellulose, which is comprised of glucose. Therefore, the hemicellulose can be deconstructed using acid hydrolysis to xylose and other $C_5$ carbohydrates, which can further be dehydrated to furfural. The cellulose and other $C_6$ carbohydrates can be deconstructed to levulinic acid in a second acid hydrolysis step that occurs simultaneously in the same reaction vessel (as shown in FIGS. 2 and 3) or in a separate reactor (as shown in FIG. 4, described below).

Referring now to FIGS. 2 and 3, a lignocellulosic feedstock 10 is introduced into reactor 12 containing an acidic reaction solvent comprising GVL, as described previously for FIG. 1. As described previously, any acid may be used to acidify the GVL reaction solution. Unlike FIG. 1, because the feedstock is lignocellulosic biomass (or any other combination of $C_5$ and $C_6$ carbohydrates), the acidic GVL solution degrades/deconstructs the cellulose (and/or other $C_6$ carbohydrates) found in the feedstock 10 to yield LA, and the xylose (and/or other $C_5$ carbohydrates) contained in the feedstock to yield furfural (Fur).

At this point, FIGS. 2 and 3 differ slightly. In FIG. 2, the product is directed via conduit 14 to separator 15 to separate the Fur from the LA in the product mix. In all of the figures, the separator 15 may be any type of separator now known or developed in the future that is dimensioned and configured to separate Fur from LA. A distillation column is suitable. The furfural/formic acid distillate exits separator 15 via conduit 19, while the remaining product, which contains LA is directed to catalytic reactor 16 via conduit 17. FIG. 3 is similar, except conduit 14 is omitted and the Fur is separated from the LA via reactive distillation using separator 15. Thus the separator 15 in FIG. 3 is integrated into the reactor 12. Again, the Fur/FA distillate exits at conduit 19, and the remaining product is directed to catalytic reactor 16 via conduit 17.

In the same fashion as described for FIG. 1, the LA present in the reaction solution exiting separator 15 may be concentrated, isolated, and/or purified and sold as the final product.

Alternatively, LA present in the product mix may be fed by conduit 17 into catalytic reactor 16, which contains a hydrogenation catalyst and my optionally include added molecular hydrogen via conduit 18. The LA present in the product mix will be hydrogenated in reactor 16 into GVL, which is removed from the reactor 16 at conduit 20. Again, the method branches at this point. The entire amount of GVL produced may be sold as the final product, or used to produce other, downstream products, such as the butene shown in the lower-right corner of FIGS. 2 and 3 at conduit 24. Or, a portion of the GVL produced may be used as the final product (or for other purposes) as shown by 24 and another portion of the GVL recycled via conduit 22 into the reactor 12.

In the same fashion as for the reaction shown in FIG. 1, the conditions in the reactor 12 and the catalyst in reactor 16 are preferably chosen to minimize the hydrogenation of GVL. The outlet 20 or reactor 16 is a stream of GVL that, as noted above, can be used as the final product chemical, or can be used to produce fuels as butene. If a mineral acid or other homogeneous acid is used in reactor 12, the acid may optionally be neutralized before the hydrogenation reaction. This is not required, but tends to increase the life of the hydrogenation catalyst present in reactor 16. Alternatively, catalysts tolerant to mineral acids (as RuRe) may be used in reactor 16. In that instance, the homogeneous acid is recycled along with the GVL solvent. If a solid acid catalyst is used in reactor 12, a filtration step (to retain the solid acid catalyst within reactor 12) maybe required before introducing the product stream from reactor 12 into the hydrogenation reactor 16.

For the one-vessel process depicted in FIGS. 2 and 3, a series of experiments were conducted to convert hemicellulose to furfural in a monophasic system reaction using mineral acids, such as SA and hydrochloric acid (HCl), as well as solid acid catalysts, such as Mordenite. GVL and mixtures of GVL and water were used as the reaction solvent in reactor 12. The experiments were carried out in 10 mL glass reactors at 170° C. in a pre-heated oil bath using magnetic stifling.

In a typical experiment, approximately 6 wt % solid corn stover was added to the reactor 12. Acid concentration (using mineral acid) ranged from 0.02 to 0.1 M. The GVL and water were added to the glass reactor to reach the desired mass ratio. The glass reactor was placed in the oil bath, held for the stated time, then taken from the oil bath and cooled with an air line. A small portion of the solution was sampled. In all experiments, no solids remained in reactor 12. Table 4 presents the results of these experiments.

TABLE 4

Corn stover can be used to produce Fur and LA simultaneously (data gathered at 170° C.)

| Acid | Time (h) | Water (wt %) | Furfural Yield (%) | LA Yield (%) |
|---|---|---|---|---|
| 0.1M SA | 1.5 | 20 | 56 | 60 |
| 0.1M SA | 1.5 | 10 | 41 | 54 |
| 0.05M SA | 3 | 20 | 57 | 47 |
| 6 wt % Amberlyst 70 + 0.02M SA | 2 | 10 | 4 | 61 |

As can be seen from Table 4, yields of both Fur and LA were quite high, especially when using mineral acids.

Figure 5:
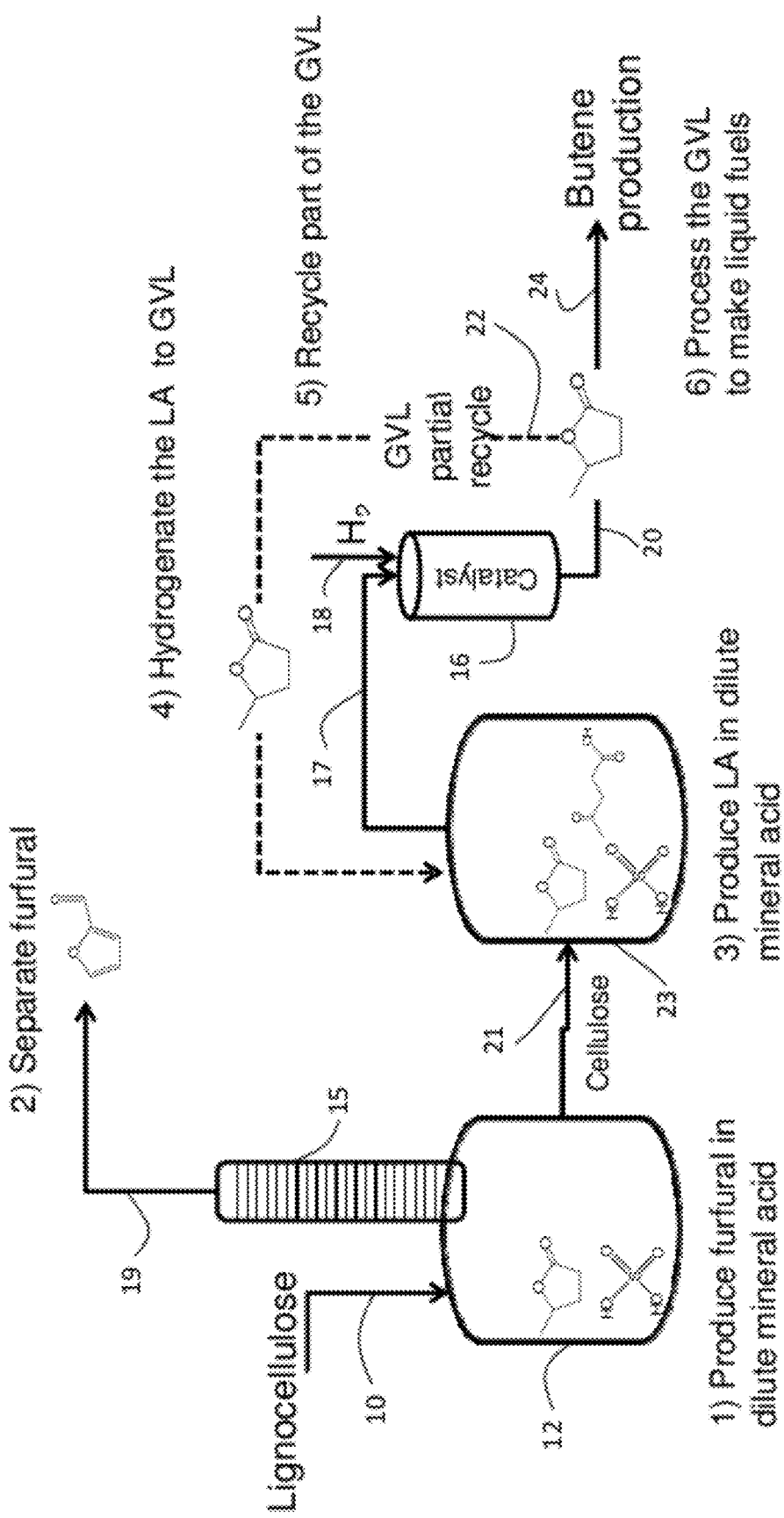
FIG. 5 is a schematic diagram illustrating a process very similar to that shown in FIG. 4, with the exception that the Fur and FA formed in monophasic reaction chamber 12 is removed via reactive distillation.

To control the process with greater precision and to optimize the conversion of xylose to furfural and cellulose to LA, the two reactions may be conducted separately, as shown in FIGS. 4 and 5. Like FIGS. 2 and 3, FIGS. 4 and 5 are identical with the exception that FIG. 5 depicts the process using a reactive separator 15, while FIG. 4 depicts the process using a stand-alone separator 15. In both of FIGS. 4 and 5, the lignocellulosic feedstock (and/or any other combination of $C_5$ and $C_6$ carbohydrates) 10 is introduced into reactor 12 as described previously. The conditions within reactor 12 (an acidic solution comprising GVL) are optimized empirically to convert xylose (and/or other $C_5$ carbohydrates) to furfural. Thus the reaction in reactor 12 is optimized to produce furfural, which is then fed to separator 15 via conduit 14 (FIG. 4) or separated from the reaction mixture via reactive separator 15 (FIG. 5).

Referring now to FIG. 4, the cellulose-(and/or other $C_6$ carbohydrates)-containing fraction exits the separator 15 at conduit 21 and is transferred to a second reactor 23. In contrast, in FIG. 5, the furfural is reactively separated as it is formed, thus the unreacted cellulose (and/or other $C_6$ carbohydrates) in the reactor 12 is directly transferred from reactor 12 to reactor 23 via conduit 21. Referring now to both FIGS. 4 and 5, in reactor 23, the solvent again comprises an acidified solution comprising GVL. This reaction solution converts cellulose (and/or other $C_6$ carbohydrates) contained in the reactants into LA. The remainder of FIGS. 4 and 5 are the same as described above for FIG. 1. The digested solution in reactor 23, which contains LA and may contain homogeneous acids, is then isolated from the reaction solution via conduit 17. At this point, the LA present in the reaction solution may be concentrated, isolated, and/or purified and sold as the final product.

Alternatively, LA present in the product mix may be fed by conduit 17 into catalytic reactor 16, which contains a hydrogenation catalyst and may optionally include added molecular hydrogen via conduit 18. The LA present in the product mix is hydrogenated in reactor 16 into GVL, which is removed from the reactor 16 at conduit 20. The method branches at this point. The entire amount of GVL produced may be sold as the final product, or used to produce other, downstream products, such as the butene shown in the lower-right corner of FIGS. 4 and 5 at conduit 24. Or, a portion of the GVL produced may be used as the final product (or for other purposes) as shown by 24 and another portion of the GVL recycled via conduit 22 into the reactor 23.

Table 5 depicts a series of experiments run using a reactor set up as shown in FIG. 4. Mineral acid was used (SA) as well as solid acids (mordenite), and combinations of the two. For the two-step process, generally a lower amount of acid is used in reactor 12 as compared to reactor 23. (See table 5, 1$^{st}$ reactor.) The lignocellulosic biomass (corn stover in the case of the reactions whose results are shown in FIG. 5) is processed in the presence of solvent comprising GVL (or comprising GVL and a small amount of water) as described previously. This yields furfural and small amounts of LA in reactor 12. Once the reaction in reactor 12 is complete, more acid is added to the solution in reactor 23 and the cellulose fraction in the biomass reactant is converted into LA. The furfural may be removed by separator 15 (preferred), or be passed along to reactor 23 (less preferred). If the furfural is not removed, product yields go down via degradation.

TABLE 5

Fur and LA yield by processing biomass sequentially. (Data at 170° C.)

| | Acid | T (° C.) | Time (h) | Water (wt %) | Furfural Yield (%) | LA Yield (%) |
|---|---|---|---|---|---|---|
| 1st Reactor (12) | 0.02M SA | 170 | 3 | 20 | 56 | 4 |
| | 0.02M SA | 170 | 16 | 20 | 62 | 5 |
| | 0.02M SA | 170 | 6 | 10 | 58 | 7 |
| | 0.02M SA | 170 | 3 | 10 | 58 | 3 |
| | 2 wt % mordenite | 170 | 2 | 10 | 82 | 16 |
| 2nd Reactor (23) | 0.1M SA[a] | 170 | 18 | 20 | 0 | 55 |
| | 0.1M SA[a] | 170 | 18 | 10 | 0 | 57 |
| | 0.2M SA[a] | 170 | 18 | 20 | 0 | 66 |
| | 2 wt % MOR + 0.02M SA[b] | 170 | 2 | 10 | 76 | 40 |
| | 2 wt % MOR + 0.02M SA[b] | 170 | 4 | 10 | 63 | 45 |
| | 2 wt % MOR + 0.05M SA[b] | 170 | 2 | 10 | 51 | 51 |
| | 2 wt % MOR + 0.1M SA[b] | 170 | 2 | 10 | 49 | 34 |

[a]0.1M SA used in the first reactor. 16 h at 170° C.
[b]2 wt % mordenite used in the first reactor. 2 h at 170° C.

As shown by the results in Table 5, the two-stage reaction is advantageous in that the two reactions (one leading to furfural, the other leading to LA) can be optimized independently from one another.

Note that in all of the reactions illustrated in FIGS. 1-5, the reactions yielding LA and/or furfural take place in monophasic reactions solutions comprising GVL or a combination of GVL and a smaller concentration of water. The reaction solvent does not partition.

Figure 6:
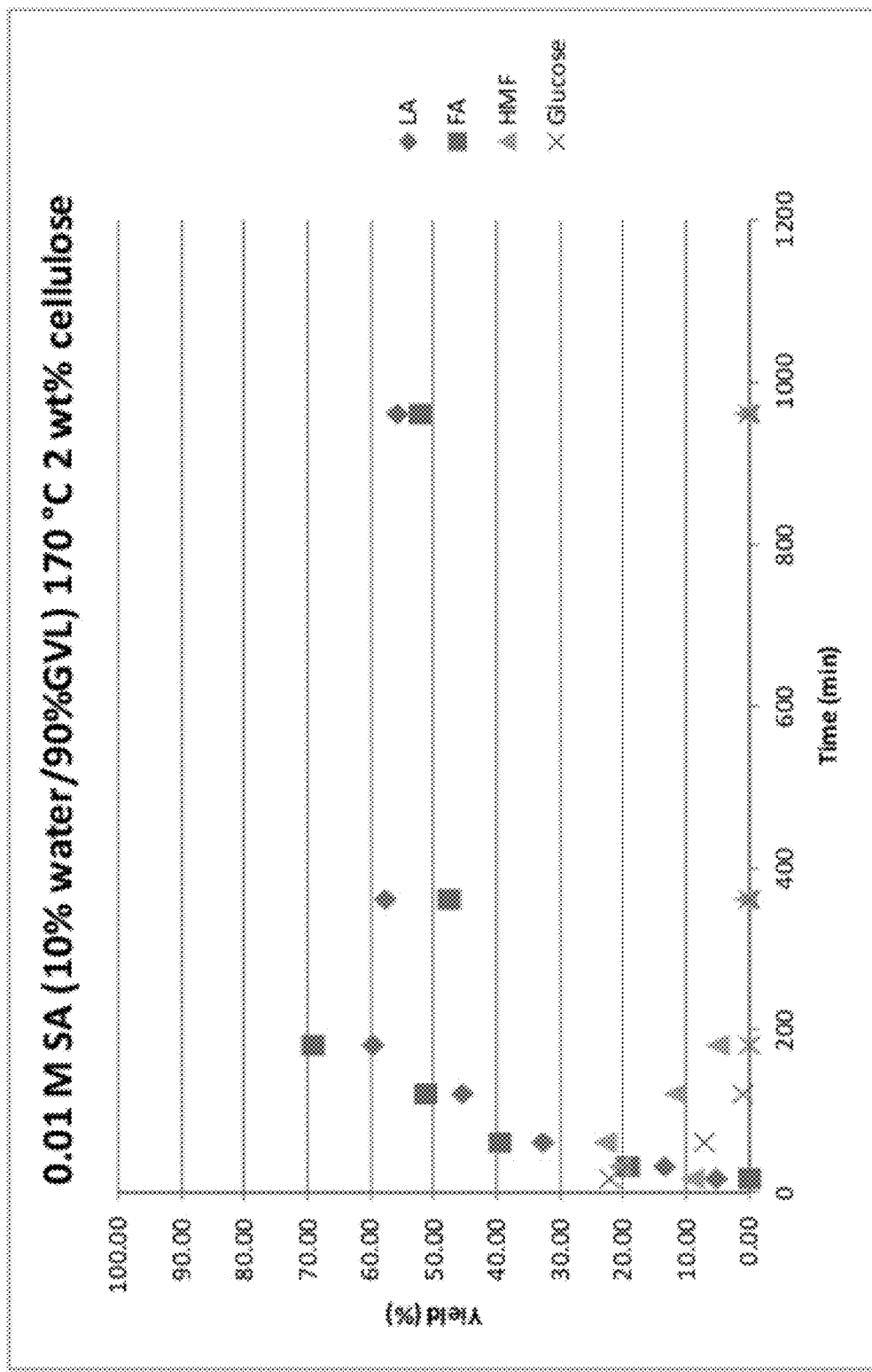
FIG. 6 is a graph depicting product yield over time for a reaction in which the solvent was 10% water/90% GVL (w/w) containing 0.01 M sulfuric acid (SA). The reactant was cellulose (2 wt %). The reaction temperature was 170° C. The monophasic reaction was carried out in a reactor 12 as depicted in FIG. 1. The X-axis depicts time in minutes; the Y-axis depicts product yield (%). Key: ♦=levulinic acid (LA). ■=formic acid (FA). ▲=hydroxymethylfurfural (HMF). ×=glucose.
Figure 7:
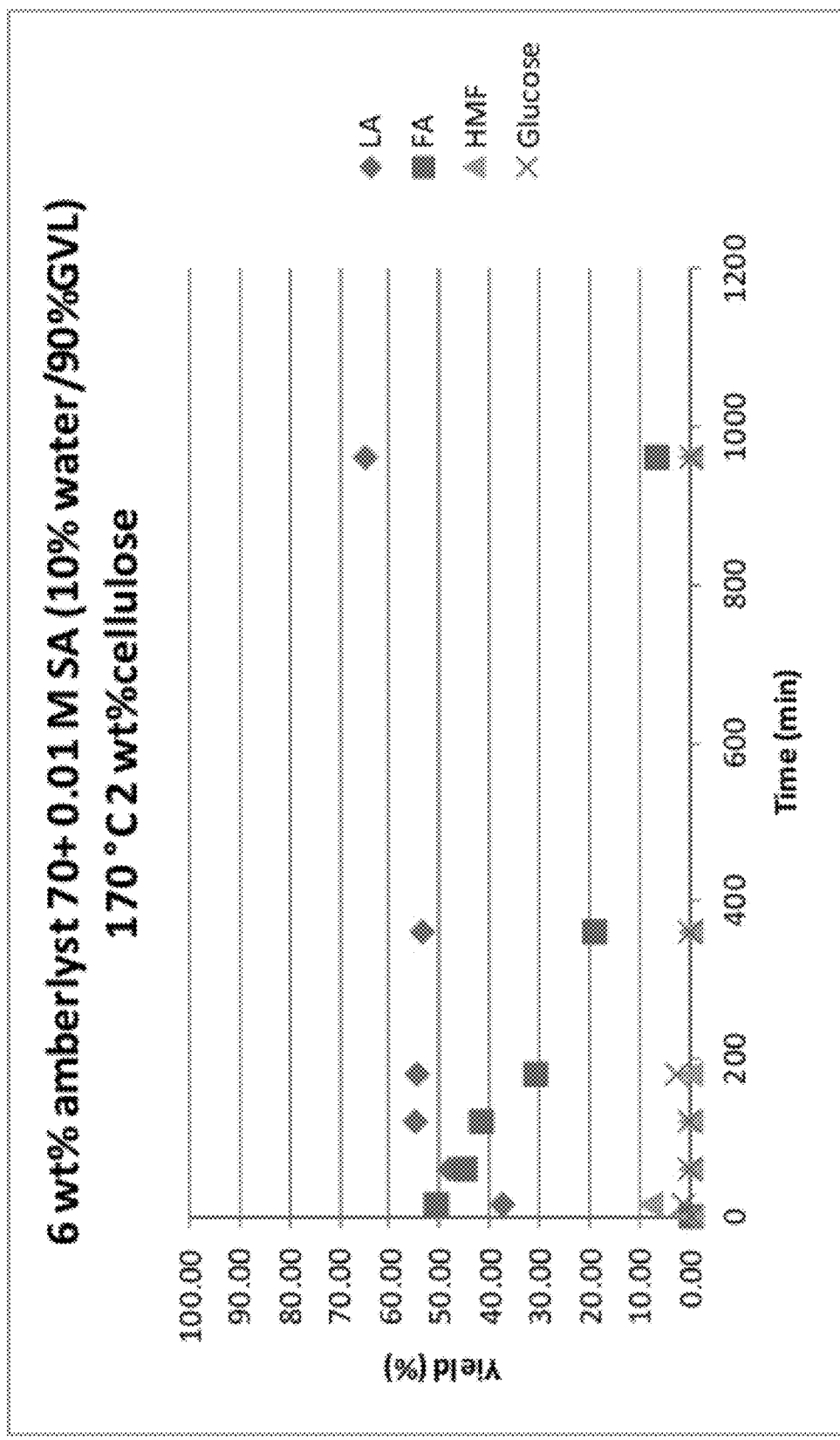
FIG. 7 is a graph depicting product yield for a reaction identical to that described in FIG. 6, with the addition of 6 wt % Amberlyst® 70-brand solid acid catalyst added to the reaction solution. All other reaction conditions were the same as recited in FIG. 6. The key is the same as in FIG. 6.

As noted previously, either homogeneous acids (such as mineral acids) and/or solid acids may be used in reactors 12 and 23. FIGS. 6 and 7 compare the product yields obtained when using a homogeneous acid (0.01 M SA in a 10% H2O/90% GVL reaction solution) versus a solid acid (6 wt % Amberlyst® 70 in a 10% H2O/90% GVL reaction solution), respectively. Thus, FIG. 6 is a graph depicting product yield over time for a reaction in which the solvent was 10% water/90% GVL (w/w) containing 0.01 M SA. The reactant was cellulose (2 wt %). The reaction temperature was 170° C. The monophasic reaction was carried out in a reactor 12 as depicted in FIG. 1. The X-axis depicts time in minutes; the Y-axis depicts product yield (%). Key: ◆=levulinic acid (LA). ■=formic acid (FA). ▲=hydroxymethylfurfural (HMF). x=glucose. FIG. 7 is a graph depicting product yield for a reaction identical to that described in FIG. 6, with the addition of 6 wt % Amberlyst® 70-brand solid acid catalyst added to the reaction solution without the presence of SA. All other reaction conditions were the same as recited in FIG. 6. The key is the same as in FIG. 6. As can be seen from the two graphs, the yield of LA is comparable whether a homogeneous acid is used or a solid acid is used.

Figure 14:
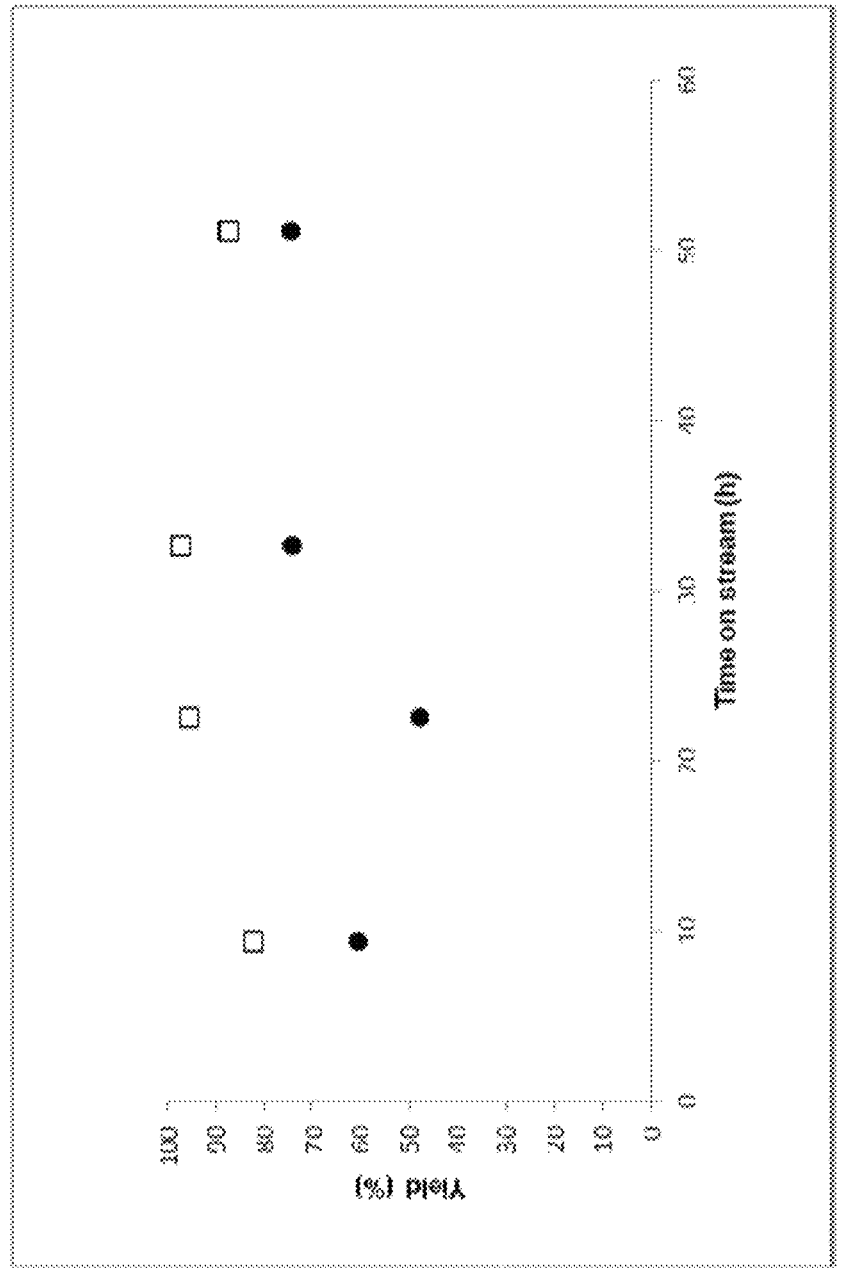
FIG. 14 is a graph depicting product yield over time for a reaction in which the solvent was 20% water/80% GVL (w/w). The reactant was furfural (0.5 wt %) and levulinic acid (0.85 wt %). Over a first catalytic bed (PtSn) at 100° C., the furfural is converted into furfuryl alcohol, while some of the levulinic acid is converted into GVL. Over a second catalytic bed (Amb-70) at 125° C., the furfuryl alcohol is converted into levulinic acid. The X-axis depicts time in minutes; the Y-axis depicts product yield (%). Key: □=furfuryl alcohol. ●=levulinic acid (LA).

The furfural, once isolated, or in presence of the levulinic acid, can be hydrogenated to furfuryl alcohol over a hydrogenation catalyst such as PtSn. Quantitative yields can be obtained at 100° C. as shown in FIG. 14. The furfuryl alcohol can be converted into levulinic acid in a second reactor over an acid catalyst such as Amberlyst 70 at high yields at 125° C., as shown in FIG. 14.

Table 6 shows the results for converting furfuryl alcohol to levulinic acid using various catalysts and reaction conditions. The feed was 1 wt % furfuryl alcohol, 2 wt % levulinic acid in GVL/water solvent 80/20 w/w.

TABLE 6

Furfuryl alcohol conversion to levulinic acid in presence of levulinic acid in GVL/water solution 80/20.

| catalyst | LA yield (%) | time (h) | temperature (° C.) |
|---|---|---|---|
| SA | 62 | 1 | 125 |
| Amb 15 | 61 | 1 | 125 |
| Mordenite | 42 | 1 | 125 |
| HZSM5 | 63 | 1 | 125 |
| Nafion | 38 | 1 | 125 |
| HZSM5 | 63 | 0.5 | 125 |
| HZSM5 | 73 | 1.5 | 125 |
| HZSM5 | 52 | 0.5 | 100 |
| HZSM5 | 60 | 1 | 100 |
| HZSM5 | 60 | 1.5 | 100 |
| HZSM5 | 75 | 1.5 | 150 |
| HZSM5 | 80 | 1 | 150 |
| HZSM5 | 72 | 0.5 | 150 |
| Amb70 | 71 | 1 | 125 |

All of the reactions described up to this point have been monophasic reactions. Another version of the process, however, uses GVL as an extracting solvent in a biphasic reaction. In this approach, a biphasic system comprising an extractive organic layer comprising of gamma-valerolactone (GVL) and an aqueous layer comprising salt, xylose (and/or other $C_5$ carbohydrates), and a mineral acid is used to convert the xylose (and/or other $C_5$ carbohydrates) to furfural. The aqueous xylose (and/or other $C_5$ carbohydrates) solution can be obtained through the dilute acid hydrolysis of biomass for deconstruction of the hemicellulose portion. Following the hydrolysis step, furfural is produced in a biphasic reactor system for xylose (and/or other $C_5$ carbohydrates) dehydration, where the furfural is extracted into the organic phase preventing its further degradation catalyzed by the mineral acid in the aqueous phase. Solvents used in the literature (e.g., toluene, methyl-isobutyl-ketone, THF, butanol, alkylphenols) have good partition coefficients; however, most of these solvents (except for alkylphenols) have lower boiling points than furfural so that the solvent must be evaporated to obtain the product. This is energy intensive because the furfural is produced in dilute solutions. In addition, all of these solvents are external solvents that need to be transported to the biorefining site.

Utilizing GVL as the extracting solvent is advantageous because (i) GVL is a green solvent that can be obtained from lignocellulose on site; (ii) the partition coefficient of furfural with salt present in the aqueous phase is high enough, 23, allowing for increased furfural concentrations; (iii) GVL has a higher boiling point compared to that of furfural, enabling recovery of furfural as the top product in distillation (assuming furfural is desired as the end product); (iv) furfural can be converted to GVL through the intermediate formation of furfuryl alcohol and levulinic acid/levulinate esters, eliminating any distillation/purification steps if GVL is desired as the end product; and (v) GVL solubilizes the humin by-products formed in the xylose dehydration reaction, facilitating the processing of these species before they form solids that plug the reactor.

Figure 8:
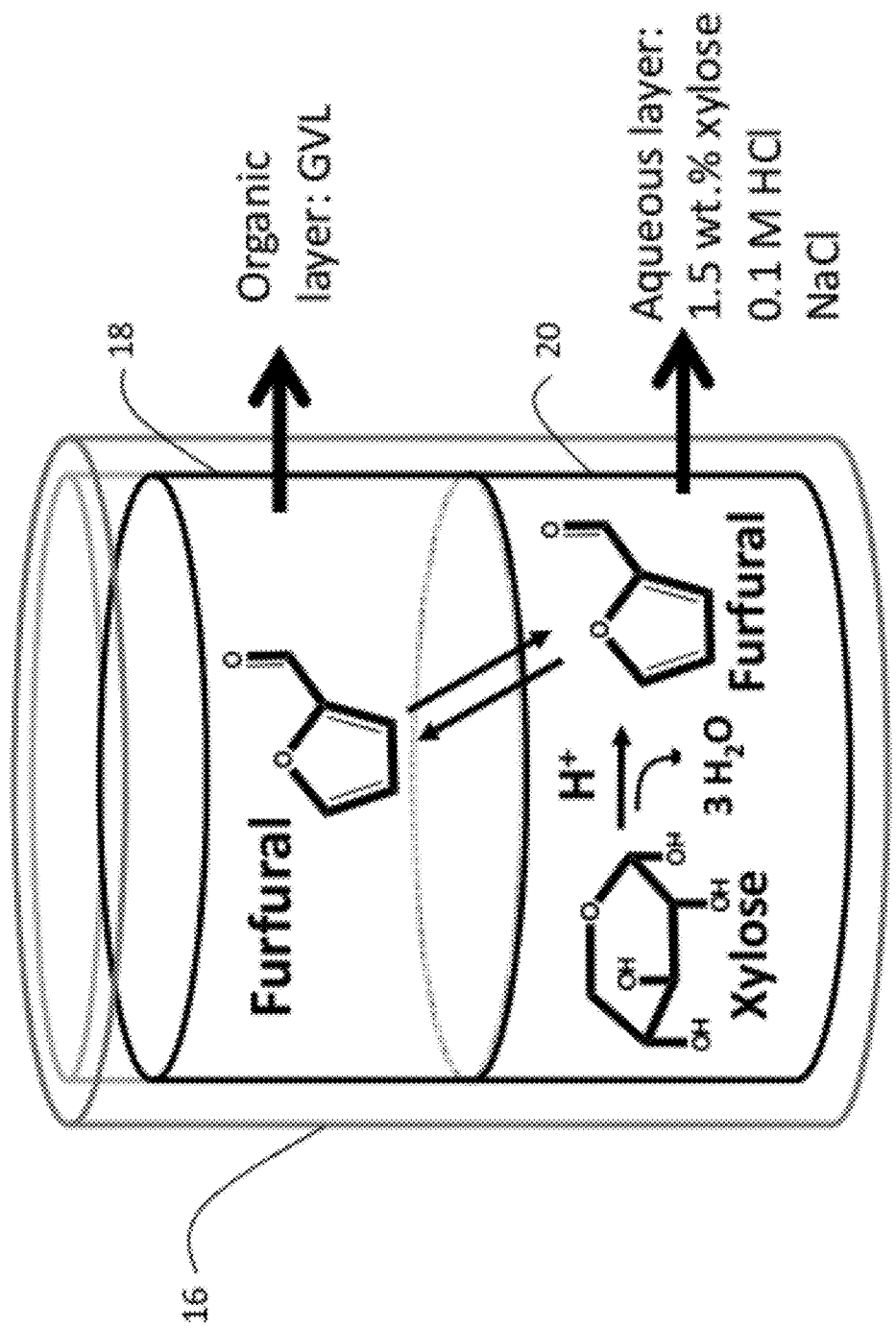
FIG. 8 is a schematic diagram illustrating the biphasic dehydration of xylose to furfural. (Xylose is derived from hemicellulosic biomass.) The upper organic layer preferably comprises GVL. The lower layer comprises an aqueous, acidic solution of xylose derived from biomass. As shown in the figure, the lower layer contains mineral acid, 1.5 wt % xylose, and is saturated with NaCl. The xylose is dehydrated into furfural, which spontaneously partitions into to the upper organic phase.

This approach is illustrated schematically in FIG. 8. Depicted in the figure is a reactor 16 containing a biphasic reaction system comprising an upper organic layer comprising GVL and a lower aqueous layer containing acid, a solute to force separation of the aqueous and organic layers (as shown in the figure, NaCl, but any non-reactive water-soluble solute will work), and the reactant xylose (and/or other $C_5$ carbohydrates). As shown in the figure, the acidic aqueous layer dehydrates the xylose (and/or other $C_5$ carbohydrates) to furfural, which then spontaneously partitions into the upper organic phase.

Experimentally, the co-inventors have used this process to achieve yields of 81% to furfural in 20 min using 2 g of 1.5 wt % xylose dissolved in 0.1 M HCl solution saturated with NaCl in contact with 2 g of GVL. In this experiment, 95% of the furfural was recovered in the GVL phase. Furfural selectivity/yield values for different xylose concentrations, type and concentration of mineral acids, and aqueous-to-organic mass ratios are shown in Table 7.

TABLE 7

Results of xylose dehydration experiments carried out at 175° C. in a biphasic reactor system (10 mL glass reactors), using GVL as the extracting solvent, with aqueous solutions containing HCl or SA and saturated with NaCl.

| Xylose wt % in the aqueous feed | Catalyst | Aq/org (g/g) | Time (min) | Xylose conversion (%) | Furfural Selectivity (%) | Furfural Yield (%) | Furfural in org (% tot) |
|---|---|---|---|---|---|---|---|
| 1.5 | 0.1M HCl | 1 | 20 | 99 | 83 | 82 | 95 |
| 1.5 | 0.1M SA | 1 | 20 | 98 | 79 | 78 | 95 |
| 3.5 | 0.1M HCl | 1 | 25 | 98 | 81 | 80 | 95 |
| 1.5 | 0.1M HCl | 2 | 20 | 99 | 81 | 80 | 91 |
| 1.5 | 0.01M HCl | 1 | 85 | 79 | 75 | 60 | 95 |
| 1.5 | 0.01M HCl | 1 | 205 | 99 | 75 | 74 | 95 |

Table 8 shows the effect of the presence of a small amount of glucose in the xylose feed due to carry over from the hemicellulose deconstruction step. As seen in Table 8, starting with a feed of 3.5 wt % xylose and 0.8% glucose in 0.1 M HCl, NaCl saturated aqueous solution, the complete conversion of glucose takes a longer time (60 min) than xylose conversion. By the time glucose is completely converted, furfural starts degrading. Glucose is converted to hydroxymethylfurfural (HMF) as well as equal molar amounts of levulinic and formic acids. In order for HMF to be converted to levulinic and formic acids, longer times (90 min) are required, at which point furfural degradation becomes more pronounced.

TABLE 8

Results of xylose and glucose dehydration experiments carried out at 175° C. in a biphasic reactor system (10 mL glass reactors), using GVL as the extracting solvent (2 g), with an aqueous solution (2 g) containing 3.5 wt % xylose, 0.8 wt % glucose, 0.1M HCl and saturated with NaCl.

| | Conversion (%) | | Yield (%) | | |
|---|---|---|---|---|---|
| | | | Xylose products (yield based on xylose) | Glucose products (yields based on glucose) | |
| Time (min) | Xylose | Glucose | Furfural | LA/FA | HMF |
| 23 | 99 | 90 | 79 | 38 | 38 |
| 35 | 100 | 96 | 77 | 48 | 32 |
| 60 | 100 | 99 | 75 | 55 | 20 |
| 90 | 100 | 100 | 69 | 71 | 3 |

The biphasic xylose dehydration step can be integrated in a biorefining strategy starting from deconstruction of hemicellulose in an aqueous dilute mineral acid solution, as shown schematically in FIG. 9. The GVL and furfural containing organic phase 18 generally will also contain HCl and NaCl. Depending on the nature of the separator 15, neutralization of the acid might be required prior to separation of the furfural from the GVL.

Referring to FIG. 9, biomass (and/or any other combination of $C_5$ and $C_6$ carbohydrates) 10 is first deconstructed in reactor 12 to yield xylose (and/or other $C_5$ carbohydrates) and glucose (and/or other $C_6$ carbohydrates), which are transferred to reactor 16 via conduit 14. Undigested cellulose (and/or other $C_6$ carbohydrates) and lignin are removed from reactor 12 via conduit 21. Reactor 16 is the same as described for FIG. 8. Inside the reactor 16 is an upper organic layer 18 comprised of GVL and a lower, acidic aqueous layer 20 with a solute dissolved therein. Xylose (and/or other $C_5$ carbohydrates) present in layer 20 is dehydrated to furfural. Glucose (and/or other $C_6$ carbohydrates) present in layer 20 is converted to LA, both of which partition into the upper organic layer 18. A portion of the upper organic layer is then introduced into separator 15 (described previously) to separate the furfural from the LA and GVL. The furfural exits separator 15 at conduit 19, while the LA and GVL exit the separator at conduit 24. The LA/GVL mixture is then passed into a catalytic reactor 28 (described previously), which is configured to hydrogenate the LA into GVL. The product, GVL, exits the hydrogenator at conduit 30. The GVL can be sold as the product 32. Or the GVL product stream can be separated—a portion 32 used as the end product and another portion 34 recycled back into reactor 16 to replenish the organic layer 18.

Figure 10:
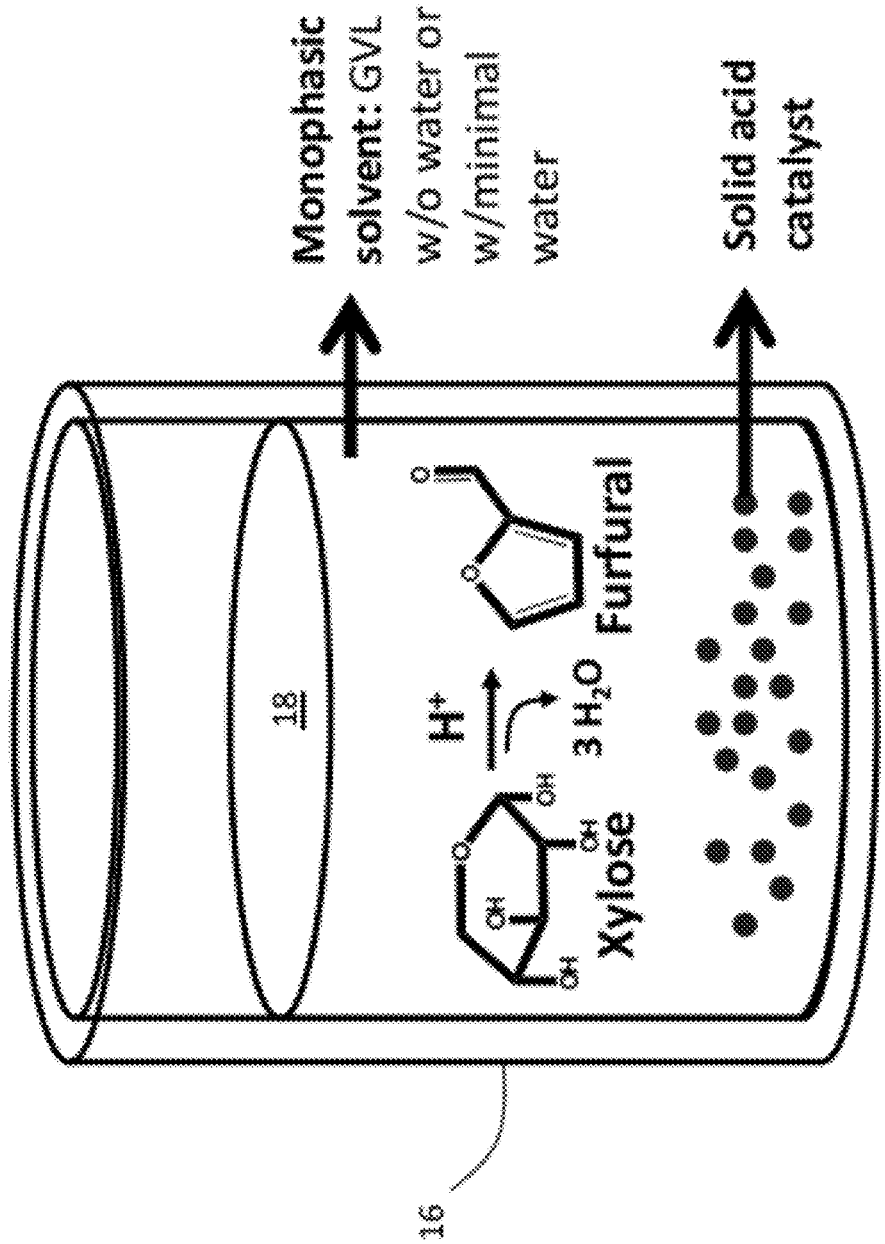
FIG. 10 is a schematic diagram illustrating monophasic dehydration of xylose to furfural. The solvent comprises GVL or a mixture of GVL and water. A solid acid catalyst is used to drive the dehydration reaction.

Another version of the process involves using the monophasic system described earlier to carry out the dehydration of xylose (and/or other $C_5$ carbohydrates) using GVL as the solvent. Using a monophasic system has certain advantages in that it eliminates the need for a liquid-liquid separation step. It also eliminates any loss of the product in the aqueous phase and the formation of emulsions between the phases. In this case, xylose (and/or other $C_5$ carbohydrates) can be obtained from the hemicellulose portion of biomass through hot water/steam or organic acid (oxalic acid) pretreatments to remove the hemicellulose portion of biomass. Xylose (and/or other $C_5$ carbohydrates) can be reacted in GVL without water or with low amounts of water using a solid acid catalyst, as shown in FIG. 10. FIG. 10 depicts schematically the dehydration of xylose (and/or other $C_5$ carbohydrates) to furfural in a monophasic system using a solvent comprising GVL and a solid acid catalyst. Shown in the figure is a reactor 16 containing a monophasic reaction solvent 18 comprising GVL. A solid acid catalyst is also within the reactor.

The use of a solid acid catalyst eliminates the complication of separating furfural from a homogenous mineral acid catalyst. In addition, minimization of the water in the reaction enables the use of solid catalysts with marginal or no leaching of acid sites. It also decreases the rate of furfural degradation reactions. Similar to the biphasic case, furfural can be separated from GVL (via distillation or any other means now known or developed in the future). Alternatively, furfural can be converted to GVL (via furfuryl alcohol and levulinic acid/levulinate esters), which can be used as the end product without any further separation or purification steps. Importantly, GVL solubilizes the humin by-products formed in the xylose dehydration reaction, thus eliminating the need to separate solid humins from the solid acid catalyst.

Figure 11:
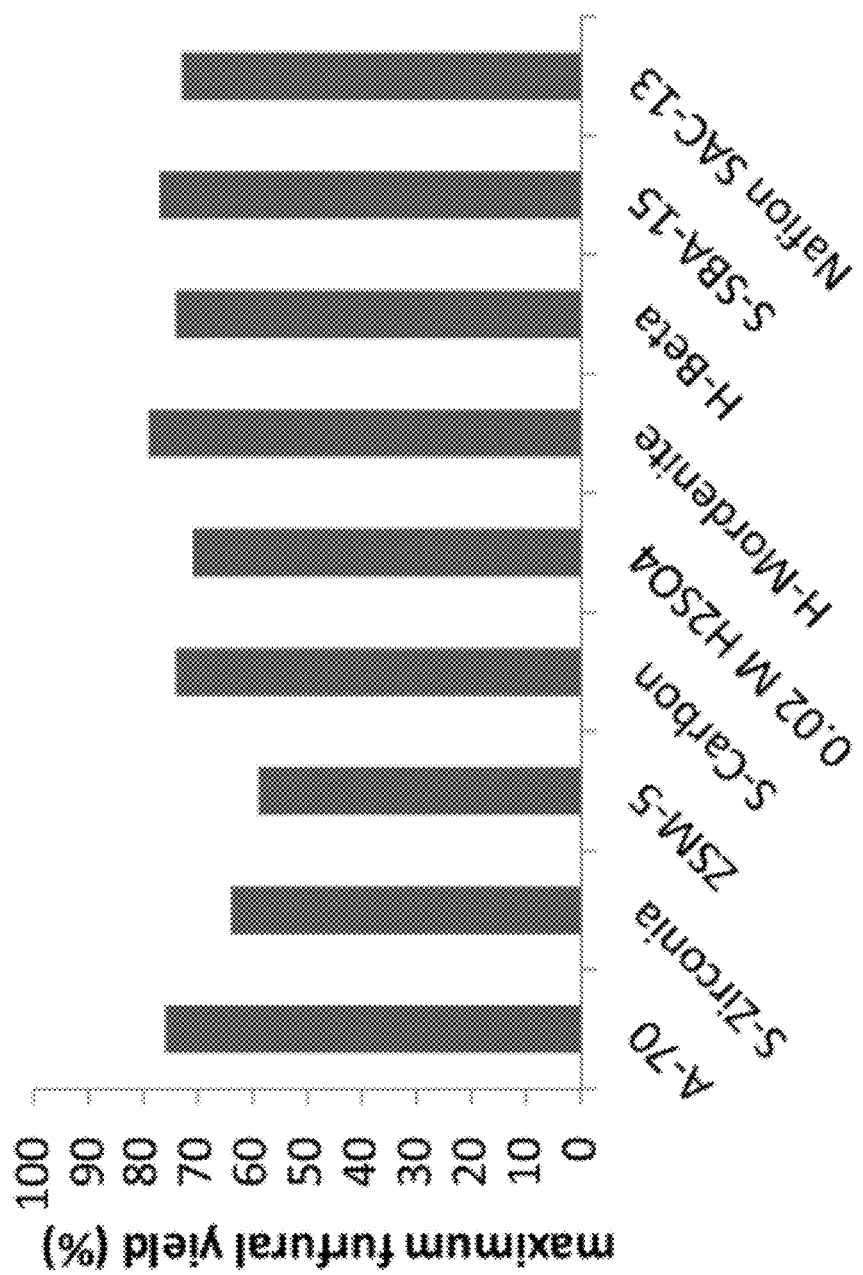
FIG. 11 is histogram depicting the furfural yield (%) of the reaction described in FIG. 10 as a function of the acid catalyst utilized.

Experimentally, yields of 71% to furfural have been obtained in 20 min using 0.08 g of xylose dissolved in 3.9 g of GVL, and using 0.05 g of a sulfated carbon catalyst. The catalyst was easily recovered and reutilized 3 times with no lose in yield. A 77% yield of furfural was obtained in 55 min using 0.08 g of xylose dissolved in 3.9 g of GVL with 0.15 g of another acidic zeolite catalyst. The catalyst was easily recovered and regenerated through calcination. Furfural yields achieved for nine (9) different acid catalysts are shown in FIG. 11.

Figure 12:
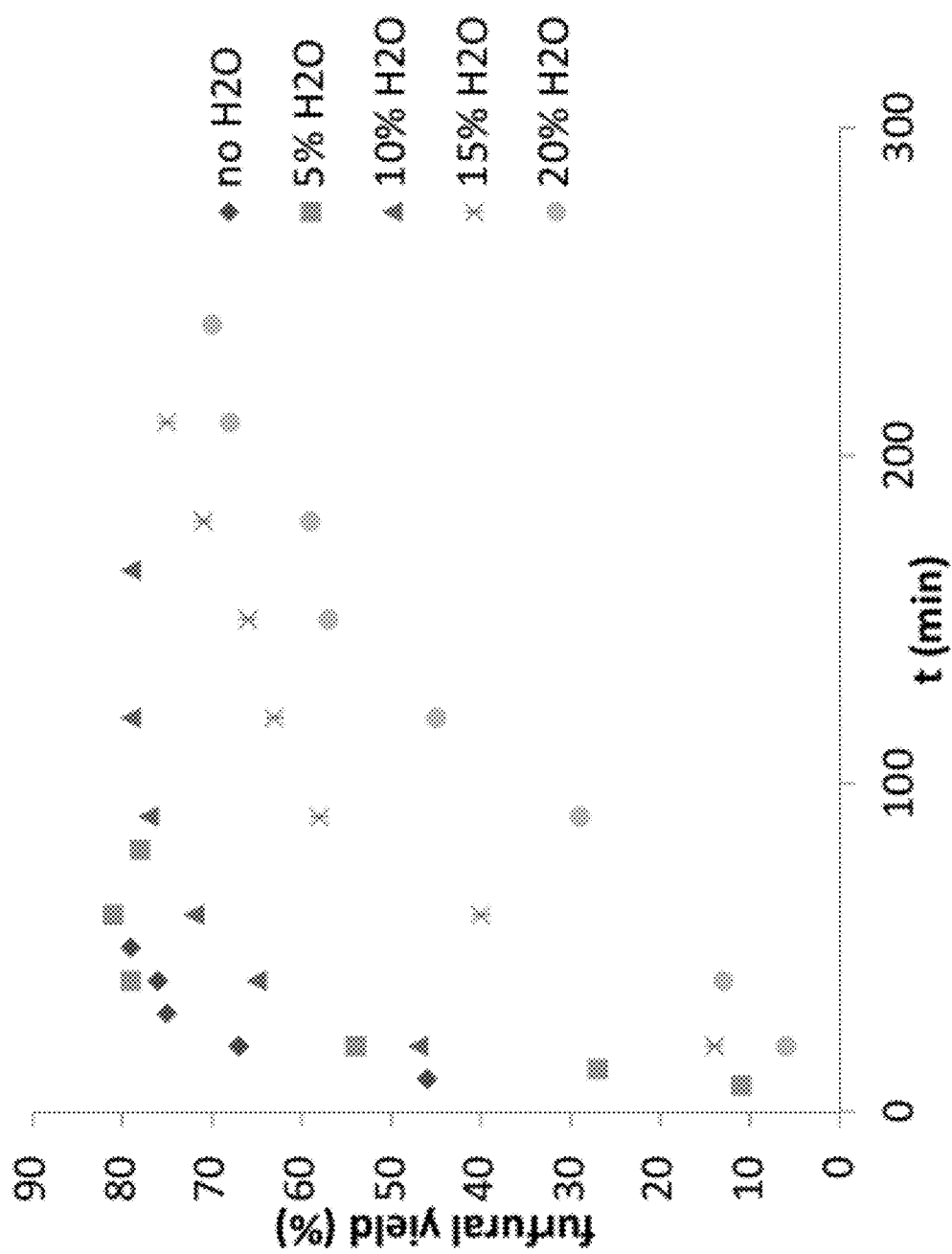
FIG. 12 is a graph depicting furfural yield (%) of the reaction described in FIG. 10 as a function of the percent water (w/w) in the mixed GVL/$H_2O$ reaction solvent. The reactant was xylose (2 wt %). The acid catalyst used was mordenite. The reaction temperature was 175° C. The X-axis depicts time in minutes; the Y-axis depicts furfural yield (%). Key: ♦=no $H_2O$. ■=5% $H_2O$. ▲=10% $H_2O$. ×=15% $H_2O$. ●=20% $H_2O$.

Among these acid catalysts, zeolites in general are also of particular interest due to their low cost and potential for regeneration with a calcination treatment following deactivation. The effect of the presence of water on the rate of furfural formation and the maximum furfural yield achievable are shown in FIG. 12. FIG. 12 depicts furfural yield as a function of reaction time using reaction solutions having various amounts of water in GVL (w/w). As shown in the figure, a small amount of water, approximately 5%, gave the highest yields in the shortest amount of time.

Table 9 shows the effect of the presence of a residual amount of glucose in the xylose feed due to carry over from the hemicellulose deconstruction step in a monophasic system that has 10% water in GVL and over H-mordenite catalyst. (Mordenite is available commercially from a large number of suppliers, such as Zeolyst International, Conshohocken, Pa.) It was found that over H-mordenite catalyst, glucose could be converted to furfural as well as HMF and levulinic/formic acids. The results of a series of experiments are presented in Table 9.

TABLE 9

Results of xylose and glucose dehydration experiments carried out at 175° C. in a monophasic reactor system (10 mL glass reactors), containing 2 wt % xylose and 10 wt % $H_2O$ in GVL (4 g) with 0.15 g H-mordenite.

| | | | Yield (%) | | | |
|---|---|---|---|---|---|---|
| | Conversion (%) | | Xylose products (yield based on xylose) | Glucose products (yields based on glucose) | | |
| Time (min) | Xylose | Glucose | Furfural | LA/FA | HMF | Furfural |
| 120 | 99 | 67 | 80 | 10 | 11 | 21 |
| 180 | 100 | 87 | 82 | 13 | 15 | 29 |
| 300 | 100 | 91 | 78 | 14 | 14 | 33 |

The monophasic, solid acid catalyzed xylose (and/or other $C_5$ carbohydrates) dehydration step can also be integrated into a biorefining strategy carried out in a dissolving pulp production facility, where hemicellulose is deconstructed by a hot water/steam treatment to produce the pre-hydrolysis liquor (PHL) as shown in FIG. 13. Here, biomass 10 is deconstructed in reactor 12. In this strategy, most of water is evaporated before the dehydration step and recycled back to the hemicellulose deconstruction step via recycle conduit 17. Any small amount of water present with GVL in the xylose/glucose dehydration step can also be recovered in the distillation step (described below) and recycled back into reactor 12. Undigested cellulose and lignin is removed from reactor 12 via conduit 21.

As shown in FIG. 13, xylose and glucose exiting reactor 12 are transferred to reactor 16, which is the same as described above for FIG. 10. Xylose present in GVL solvent 18 is dehydrated to furfural in the presence of a solid acid catalyst. Glucose present in solvent is dehydrated to LA. It should be noted that the conversion of sugar oligomers (obtained in hot water/steam treatment) along with sugar monomers is not a problem for acid-catalyzed reactions, because these catalysts achieve hydrolysis of sugar oligomers to produce monomers under conditions employed for the conversion of xylose to furfural. The solvent containing furfural and LA is then introduced into separator 15 (described previously) via conduit 22 to separate the furfural from the LA and GVL. The furfural exits separator 15 at conduit 19, while the LA and GVL exit the separator at conduit 24. The LA/GVL mixture is then passed into a catalytic reactor 28 (described previously), which is configured to hydrogenate the LA into GVL. The product, GVL, exits the reactor at conduit 30. The GVL can be sold as the product 32. Or the GVL product stream can be separated—a portion 32 used as the end product and another portion 34 recycled back into reactor 16 to replenish the solvent 18 in reactor 16.

The strategies presented here can achieve the cost-effective production furfural and derivatives, such as gamma-valerolactone. Other solvents produced by the process could also be used as solvents, e.g., furfuryl alcohol, levulinic acid, levulinic esters, HMF, etc.

REFERENCES

1. E. L. Kunkes et al., *Science* 322, 417 (2008).
2. D. M. Alonso, J. Q. Bond, J. A. Dumesic, *Green Chem.* 12, 1493 (2010).
3. J. J. Bozell, G. R. Petersen, *Green Chem.* 12, 539 (2010).
4. J. J. Bozell, *Science* 329, 522 (2010).
5. J. P. Lange et al., *Angew. Chem. Inter. Ed.* 49, 4479 (2010).
6. F. M. A. Geilen et al., *Angew. Chem. Inter. Ed.* 49, 5510 (2010).
7. H. Heeres et al., *Green Chem.* 11, 1247 (2009).
8. H. Mehdi et al., *Top. Catal.* 48, 49 (2008).
9. J. J. Bozell et al., *Resour. Conserv. Recy.* 28, 227 (2000).
10. L. Deng, J. Li, D. M. Lai, Y. Fu, Q. X. Guo, *Angew. Chem. Int. Ed.* 48, 6529 (2009).
11. Z. P. Yan, L. Lin, S. J. Liu, *Energ. fuel* 23, 3853 (2009).
12. I. T. Horvath, H. Mehdi, V. Fabos, L. Boda, L. T. Mika, *Green Chem.* 10, 238 (2008).
13. J. Q. Bond, D. M. Alonso, D. Wang, R. M. West, J. A. Dumesic, *Science* 327, 1110 (2010).
14. J. P. Lange, J. Z. Vestering, R. J. Haan, *Chem. Commun.*, 3488 (2007).
15. D. Fegyverneki, L. Orha, G. Lang, I. T. Horvath, *Tetrahedron* 66, 1078 (2010).
16. S. W. Fitzpatrick. U.S. Pat. No. 5,608,105 (1997).
17. J. C. Serrano-Ruiz, D. J. Braden, R. M. West, J. A. Dumesic, *Appl. Catal. B-Environ.* 100, 184 (2010).
18. D. J. Braden, thesis, UW-Madison (2010).

19. Kirk-Othmer Encyclopedia of Chemical Technology (Ed Wiley, New York 2000) vol. 2, pp. 203-232.
20. B. A. Riguetto et al., *Appl. Catal. Gen.* 318, 70 (2007).
21. J. Springerova, P. Kacer, L. Cerveny, *Res. Chem. Intermediat.* 31, 785 (2005).
22. See Examples and figures.
23. J. Horvat, B. Klaic, B. Metelko, V. Sunjic, *Tetrahedron Lett.* 26, 2111 (1985).
24. C. Fellay, P. J. Dyson, G. Laurenczy, *Angew. Chem. Int. Edit.* 47, 3966 (2008).
25. M. R. Prairie, A. Renken, J. G. Highfield, K. R. Thampi, M. Gratzel, *J. Catal.* 129, 130 (1991).
26. G. W. Huber, J. W. Shabaker, J. A. Dumesic, *Science* 300, 2075 (2003).
27. C. G. Liu, C. E. Wyman, *Ind. Eng. Chem. Resear.* 42, 5409 (2003).

What is claimed is:

1. A method to make levulinic acid (LA), furfural, furfuryl alcohol, or gamma-valerolactone (GVL), the method comprising:
    (a) reacting in a first reactor a reactant comprising $C_5$ carbohydrates, $C_6$ carbohydrates, cellulose, or hemicellulose, or combinations thereof in: (i) a monophasic reaction medium comprising GVL and an acid; or (ii) a biphasic reaction system comprising an organic layer comprising GVL, and a substantially immiscible aqueous layer comprising water, an acid, and a sufficient concentration of a water-soluble solute to yield an aqueous solution that is substantially immiscible with the organic layer;
    (b) wherein at least a portion of $C_5$ carbohydrates, if present in the reactant, is converted into furfural, and at least a portion of $C_6$ carbohydrates, if present in the reactant, is converted to LA.

2. The method of claim 1, wherein the acid in (a)(i) and (a)(ii) is independently selected from the group consisting of solid acids, hydrochloric acid, nitric acid, phosphoric acid, sulfuric acid, boric acid, hydrofluoric acid, trifluoroacetic acid, hydrobromic acid, acetic acid, oxalic acid, toluenesulfonic acid, and Lewis acids.

3. The method of claim 2, wherein the acid in (a)(i) and (a)(ii) is a solid acid.

4. The method of claim 3, wherein the solid acid is a zeolite.

5. The method of claim 1, wherein the water-soluble solute in (a)(ii) is a water-soluble salt, monosaccharide, disaccharide, or trisaccharide.

6. The method of claim 5, wherein the water-soluble solute is sodium chloride or fructose.

7. The method of claim 5, wherein the water-soluble salt is sodium chloride.

8. The method of claim 7, wherein the sodium chloride is present in a concentration of from about 6 wt % to about 35 wt % (saturation), based on the weight of the water in the aqueous solution.

9. The method of claim 1, further comprising:
    (c) converting at least a portion of any LA formed in step (b) into GVL.

10. The method of claim 9, wherein step (c) comprises converting the LA into GVL using a catalyst comprising one or more metals from Groups 6-14 of the periodic chart.

11. The method of claim 9, wherein step (c) comprises converting the LA into GVL using a catalyst comprising ruthenium, nickel, platinum, rhodium, tin, copper, and combinations thereof.

12. The method of claim 11, wherein the catalyst comprises ruthenium and tin.

13. The method of claim 9, further comprising:
    (d) recycling at least a portion of any GVL formed in step (c) into the reactor of step (a).

14. The method of claim 9, further comprising:
    (c) converting at least a portion of any furfural formed in step (b) into furfuryl alcohol.

15. The method of claim 14, wherein step (c) comprises converting furfural into furfuryl alcohol using a catalyst comprising one or more metals from Groups 6-14 of the periodic chart.

16. The method of claim 15, wherein step (c) comprises converting the furfural into furfuryl alcohol using a catalyst comprising ruthenium, nickel, platinum, rhodium, tin, copper, and combinations thereof.

17. The method of claim 14, wherein step (c) comprising converting at least a portion of any furfuryl alcohol formed in step (c) into levulinic acid, and further wherein the acid in steps (a)(i) and (a)(ii) is independently selected from the group consisting of solid acids, hydrochloric acid, nitric acid, phosphoric acid, sulfuric acid, boric acid, hydrofluoric acid, trifluoroacetic acid, hydrobromic acid, acetic acid, oxalic acid, toluenesulfonic acid, and Lewis acids.

18. The method of claim 14, further comprising:
    (d) converting at least a portion of any furfuryl alcohol formed in step (c) into levulinic acid.

19. The method of claim 18, wherein step (d) comprises converting the furfuryl alcohol into levulinic acid using a solid acid catalyst.

20. The method of claim 1, wherein step (a) comprises reacting the reactant in a monophasic reaction medium, and further comprising:
    (c) separating at least a portion of the furfural, if present, from the reaction medium; and
    (d) converting at least a portion of the LA, if present, into GVL.

21. The method of claim 20, further comprising:
    (e) converting at least a portion of any furfural from step (c) into furfuryl alcohol.

22. The method of claim 21, further comprising:
    (f) converting at least a portion of any furfuryl alcohol from step (e) into levulinic acid.

23. The method of claim 20, further comprising, after step (d)
    (e) recycling at least a portion of the GVL formed in step (d) into the reactor of step (a).

24. The method of claim 1, wherein step (a) comprises reacting the reactant in a first reactor in the monophasic reaction medium comprising GVL and an acid, wherein at least a portion of $C_5$ carbohydrates, if present in the reactant, is converted into furfural, and then transferring at least a portion of the monophasic reaction medium comprising GVL and an acid to a second reactor, wherein at least a portion of $C_6$ carbohydrates, if present in the reactant, is converted to LA.

25. The method of claim 24, wherein the acid is selected from the group consisting of solid acids, hydrochloric acid, nitric acid, phosphoric acid, sulfuric acid, boric acid, hydrofluoric acid, trifluoroacetic acid, hydrobromic acid, acetic acid, oxalic acid, toluenesulfonic acid, and Lewis acids.

26. The method of claim 25, wherein the acid in (a)(i) and (a)(ii) is a solid acid.

27. The method of claim 26, wherein the solid acid is a zeolite.

28. The method of claim 24, further comprising separating at least a portion of any furfural formed in the first reactor from the reaction medium before the reaction medium is transferred to the second reactor.

29. The method of claim 24, further comprising converting at least a portion of any furfural formed in the first reactor into furfuryl alcohol before the reaction medium is transferred to the second reactor.

30. The method of claim 29, further comprising converting at least a portion of any furfuryl alcohol formed into levulinic acid before the reaction medium is transferred to the second reactor.

31. The method of claim 30, further comprising converting at least a portion of any levulinic acid formed into GVL before the reaction medium is transferred to the second reactor.

32. The method of claim 24, further comprising converting at least a portion of the LA contained in the second reactor into GVL.

33. The method of claim 32, further comprising recycling at least a portion of the GVL into the second reactor.

34. The method of claim 1, wherein step (a) comprises reacting the reactant in a first reactor in the biphasic reaction system, wherein, at least a portion of any $C_5$ carbohydrates in the reactant is converted to furfural, and at least a portion of the furfural so formed partitions into the organic layer.

35. The method of claim 34, further comprising separating at least a portion of any furfural in the organic layer from the organic layer.

36. The method of claim 34, further comprising converting at least a portion of the furfural into furfuryl alcohol.

37. The method of claim 36, further comprising converting at least a portion of the furfuryl alcohol into levulinic acid.

38. The method of claim 37, further comprising converting at least a portion of the levulinic acid into GVL.

39. The method of claim 34, wherein the reactant comprises xylose and glucose, and wherein, at least a portion of the glucose is converted into LA, and then separating the LA from the furfural.

40. The method of claim 39, further comprising converting at least a portion of the LA into GVL.

41. The method of claim 40, further comprising recycling at least a portion of the GVL into the first reactor.

42. The method of claim 34, wherein the acid is selected from the group consisting of solid acids, hydrochloric acid, nitric acid, phosphoric acid, sulfuric acid, boric acid, hydrofluoric acid, trifluoroacetic acid, hydrobromic acid, acetic acid, oxalic acid, toluenesulfonic acid, and Lewis acids.

* * * * *